(12) United States Patent
Thompson et al.

(10) Patent No.: US 7,025,732 B2
(45) Date of Patent: Apr. 11, 2006

(54) BIOPSY DEVICE WITH VARIABLE SPEED CUTTER ADVANCE

(75) Inventors: Bennie Thompson, Cincinnati, OH (US); Beth McCombs, Cincinnati, OH (US); John Hunt, Cincinnati, OH (US); John Kretcham, Cincinnati, OH (US); John A. Hibner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/785,755

(22) Filed: Feb. 24, 2004

(65) Prior Publication Data

US 2004/0249307 A1 Dec. 9, 2004

Related U.S. Application Data

(60) Provisional application No. 60/449,970, filed on Feb. 25, 2003.

(51) Int. Cl.
*A61B 10/00* (2006.01)

(52) U.S. Cl. .................. 600/564; 600/568; 606/167

(58) Field of Classification Search ............ 600/562, 600/564–568; 606/167, 168, 170, 171
See application file for complete search history.

(56) References Cited

U.S. PATENT DOCUMENTS

| 4,767,601 A | 8/1988 | Kuerzinger et al. |
| 4,783,317 A | 11/1988 | Kuerzinger et al. |
| 4,940,061 A * | 7/1990 | Terwilliger et al. ......... 600/567 |
| 5,167,927 A | 12/1992 | Karlson |
| 5,526,822 A | 6/1996 | Burbank et al. |
| 5,628,446 A * | 5/1997 | Geiste et al. ............ 227/176.1 |
| 5,649,547 A | 7/1997 | Ritchart et al. |
| 5,769,086 A | 6/1998 | Ritchart et al. |
| 5,775,333 A | 7/1998 | Burbank et al. |
| 5,780,715 A | 7/1998 | Imblum |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,010,476 A * | 1/2000 | Saadat ..................... 604/22 |
| 6,017,316 A | 1/2000 | Richart et al. |
| 6,077,230 A | 6/2000 | Gregoire et al. |
| 6,086,544 A | 7/2000 | Hibner et al. |
| 6,120,462 A | 9/2000 | Hibner et al. |

(Continued)

FOREIGN PATENT DOCUMENTS

DE 42 12 910 10/1993

(Continued)

OTHER PUBLICATIONS

U.S. Appl. No. 10/785,756, filed Feb. 24, 2004, Thompson et al.

(Continued)

*Primary Examiner*—Charles Marmor

(57) ABSTRACT

A biopsy device having a translating and rotating cutter is disclosed. The translational speed of the cutter is varied using a variable pitch member. The variable pitch member can include a shaft having a relatively coarse threaded portion for rapid cutter advance and a relatively finer threaded portion for cutter advance during tissue severing.

20 Claims, 29 Drawing Sheets

U.S. PATENT DOCUMENTS

| | | | |
|---|---|---|---|
| 6,228,055 B1 | 5/2001 | Forester et al. | |
| 6,231,522 B1 | 5/2001 | Voegele et al. | |
| 6,273,862 B1 | 8/2001 | Privitera et al. | |
| 6,402,701 B1 * | 6/2002 | Kaplan et al. | 600/567 |
| 6,428,487 B1 * | 8/2002 | Burdorff et al. | 600/568 |
| 6,585,664 B1 * | 7/2003 | Burdorff et al. | 600/564 |
| 6,638,235 B1 * | 10/2003 | Miller et al. | 600/566 |
| 6,712,774 B1 * | 3/2004 | Voegele et al. | 600/567 |

FOREIGN PATENT DOCUMENTS

| | | |
|---|---|---|
| EP | 0 178 507 | 4/1986 |
| EP | 0 262 670 | 4/1988 |
| GB | 2 191 585 | 12/1987 |

OTHER PUBLICATIONS

EPO Search Report dated May 21, 2001 for corresponding patent application, European Patent Application No. EP 00 31 1425.

International Search Report dated Mar. 10, 2005 for corresponding patent application, International Patent Application No. PCT/US04/05381.

* cited by examiner

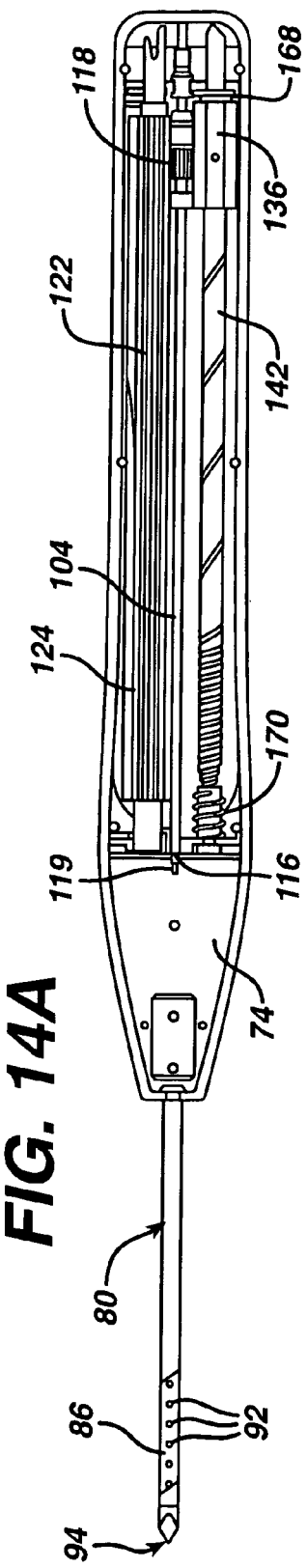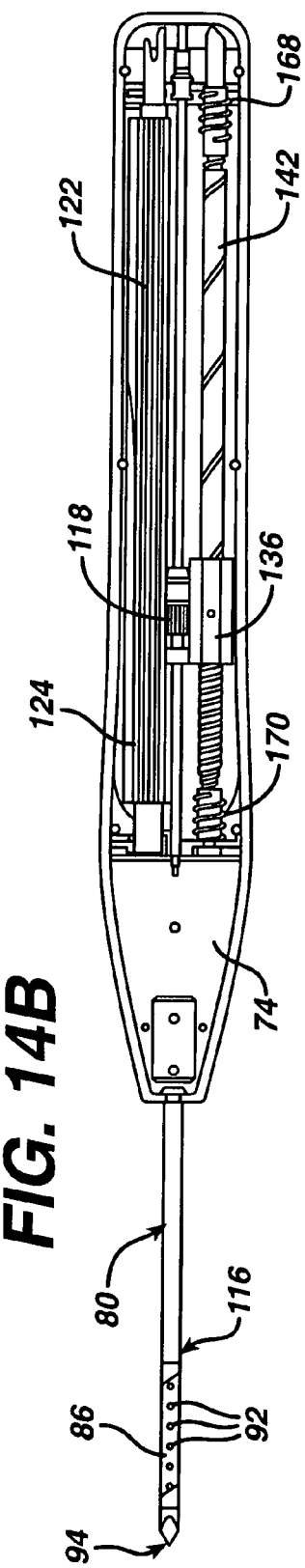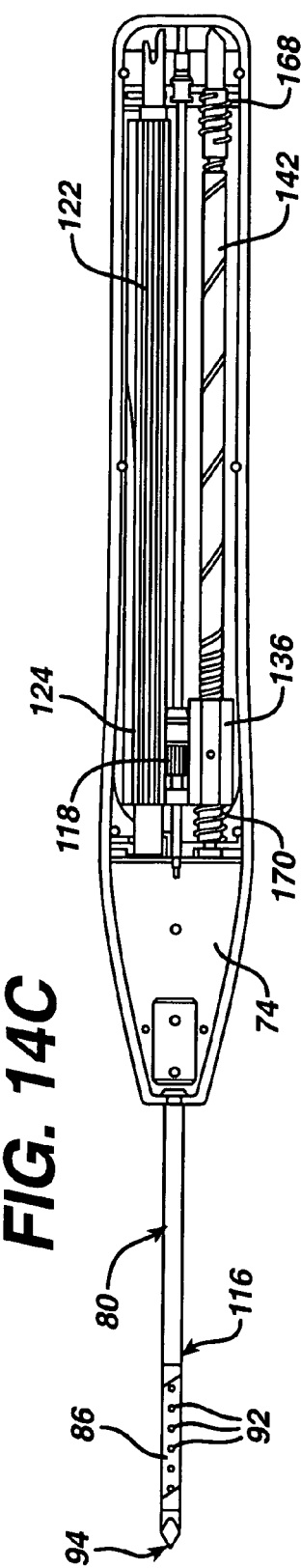

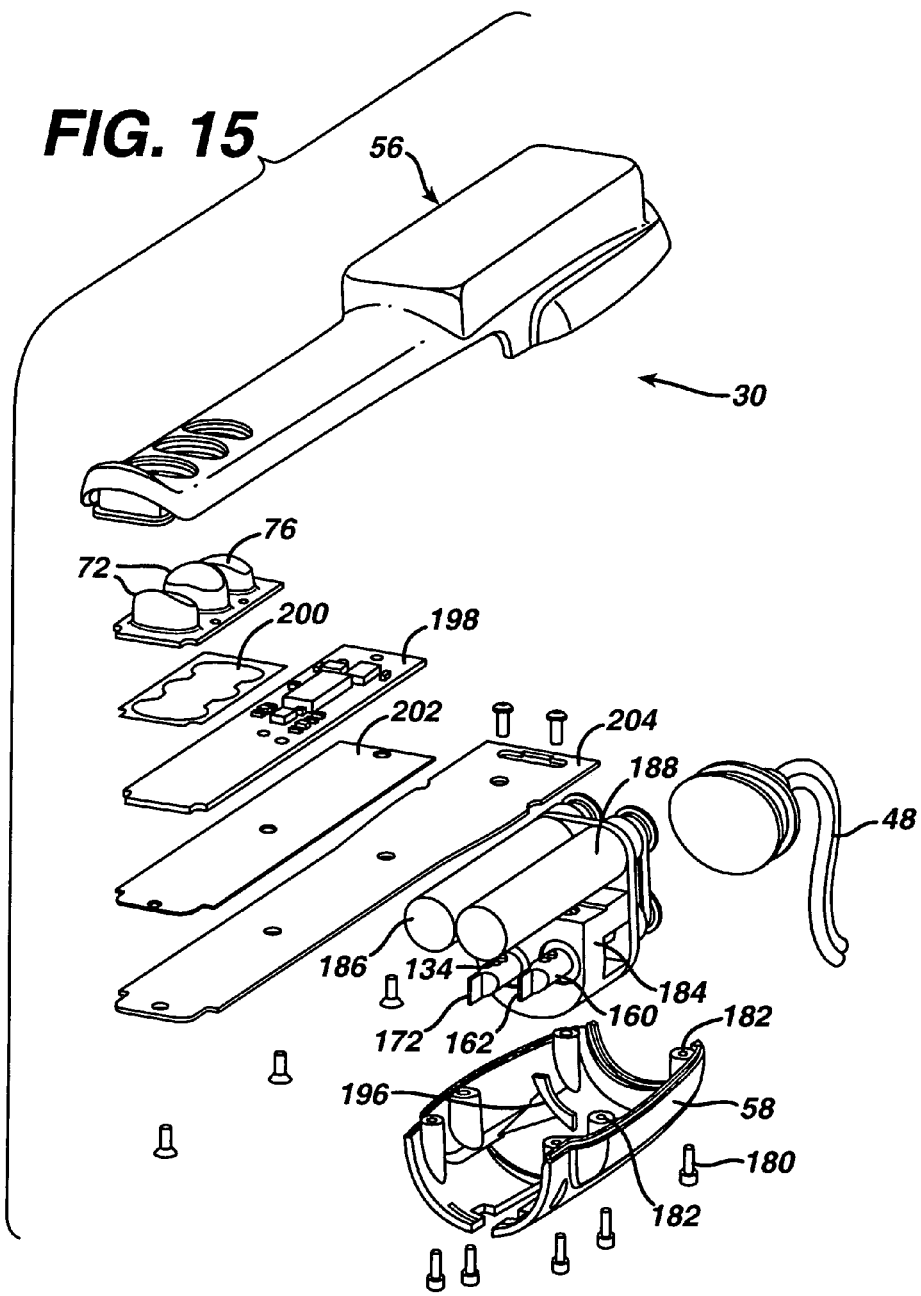

BIOPSY DEVICE WITH VARIABLE SPEED CUTTER ADVANCE

This application claims priority to provisional patent application Ser. No. 60/449,970 filed Feb. 25, 2003.

FIELD OF THE INVENTION

The present invention relates in general to biopsy devices and, more particularly, to methods and devices for advancing and driving a cutter in a biopsy device.

BACKGROUND OF THE INVENTION

The diagnosis and treatment of patients with cancerous tumors is an ongoing area of investigation. Medical devices for obtaining tissue samples for subsequent sampling are known in the art. For instance, a biopsy instrument now marketed under the trade name MAMMOTOME is commercially available for use in obtaining breast biopsy samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; US 2003/0199785 published Oct. 23, 2003; US 2003/0199754 published Oct. 23, 2003; US 2003/0199754 published Oct. 23, 2003.

SUMMARY OF THE INVENTION

It can be desirable to vary the translational speed of a rotating and translating cutter in a biopsy device. For instance, it may be desirable to have the cutter translate at different rates. By way of example, U.S. Pat. No. 6,120,462 discloses a method for controlling a biopsy device.

While motor speed can be varied corresponding to a desired variation in translational speed of a cutter, it may be undesirable to require operation of a motor at significantly different speeds, or to incorporate complex controls for varying a motor speed. A transmission assembly having a gear train could be employed to vary a cutter translation speed, but such an approach may add undesired complexity or weight to the biopsy device.

In one embodiment, the present invention provides a biopsy device comprising a cannula having a tissue receiving port; a tissue cutter disposed coaxially with the cannula, the cutter adapted for translation relative to the cannula; and a variable pitch member operatively associated with the tissue cutter for providing variation in the translational speed of the tissue cutter. The tissue cutter can be adapted for translation and rotation within the cannula during a portion of the cutter travel. A motor, such an electric motor, can be employed for rotating the variable pitch member. The motor can provide rotation at a desired speed, and the variable pitch member can be employed to vary the translational speed of the cutter independently of the rotational speed of the motor.

The variable pitch member can be in the form of a variable pitch rotation shaft having a threaded portion of varying pitch for providing a variable pitch cam surface. The biopsy device can be a handheld device which includes a first motor for providing rotation of the variable pitch member and a second motor for providing rotation of the cutter. The variable pitch rotation shaft can include a relatively coarse pitch portion for advancing the cutter at a relatively rapid rate prior to tissue cutting, and a relatively fine pitch portion for advancing the cutter at a relatively slower rate during tissue cutting.

The variable pitch cam surface of the variable pitch rotation shaft can be in the form of a cam slot formed in the outer surface of the shaft. A cam nut can be supported on the rotated shaft, and can be translated along the length of the shaft at a speed that is a function of the pitch of the cam slot on the shaft. Depending on the direction of rotation of the shaft, translation of the cam nut can provide translation of the cutter in a forward (distal) or reverse (proximal) direction.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 14A is a top view of the probe assembly with the upper shell removed to reveal the cutter in a first, fully retracted position;

FIG. 14B is a top view of the probe assembly with the upper shell removed to reveal the cutter in a third position, wherein the distal end of the cutter is immediately proximal to the port;

FIG. 14C is a top view of the probe assembly with the upper shell removed to reveal the cutter in a fourth, fully deployed position;

FIG. 15 is an exploded isometric view of the holster showing a first, double motor embodiment of the present invention;

DETAILED DESCRIPTION OF THE INVENTION

Figure 1:
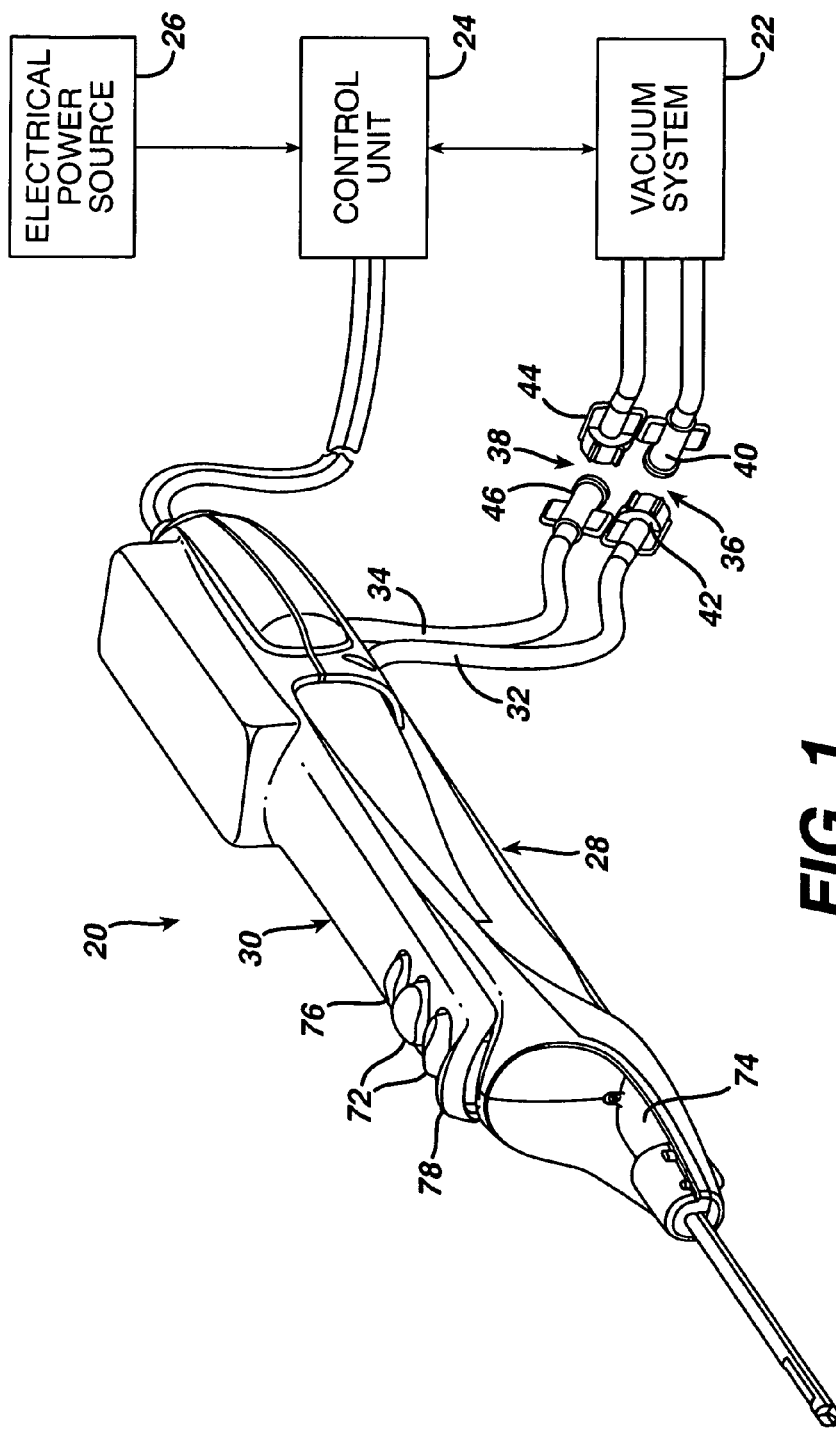
FIG. 1 is an isometric view of a biopsy instrument according to one embodiment of the present invention, which includes a handpiece for the collection of soft tissue.

The present invention pertains to a biopsy device for obtaining a tissue portion from within a body and, in particular, to controlling the speed of a cutting instrument within a core biopsy device. An example of a core biopsy device is described in U.S. Pat. No. 6,086,544 issued to Hibner et al., which is incorporated herein by reference. FIG. 1 shows a core sampling biopsy instrument according to the present invention comprising a handpiece identified generally by the numeral 20, a vacuum system 22, a control unit 24, and a power source 26. Handpiece 20 is preferably lightweight and ergonomically-shaped to be easily manipulated by an operator's hand. Handpiece 20 includes a probe assembly 28 and a detachably connected holster 30.

Probe assembly 28 is connected to vacuum system 22 by a first vacuum tube 32 and a second vacuum tube 34. First and second vacuum tubes 32, 34 are detachably connected to vacuum system 22 by a first connector 36 and a second connector 38 respectively. First connector 36 has a male portion 40 and a female portion 42 attached to first vacuum tube 32. Second connector 38 has a female portion 44 and a male portion 46 attached to second vacuum tube 34. Connector portions 40, 42, 44 and 46 are attached in this manner to prevent the accidental switching of first and second tubes 32 and 34 to vacuum system 22. Holster 30 includes a control cord 48 operationally connecting the handpiece 20 to control unit 24 and power source 26. Control cord 48 provides electrical power and control information to handpiece 20.

Because handpiece 20 is manipulated by the operator's hand rather than by an electromechanical arm, the operator may steer the tip of handpiece 20 with great freedom towards the tissue mass of interest. The surgeon has tactile feedback while doing so and can thus ascertain, to a significant degree, the density and hardness of the tissue being encountered. In addition, handpiece 20 may be held approximately parallel to the chest wall of the patient for obtaining tissue portions closer to the chest wall than may be obtained when using an instrument mounted to an electromechanical arm. Those skilled in the art may appreciate that a mount or "nest" could be provided to hold handpiece 20 securely to the movable arm of an X-ray stereotactic table in the event that it is desirable to use an X-ray stereotactic table.

Figure 2:
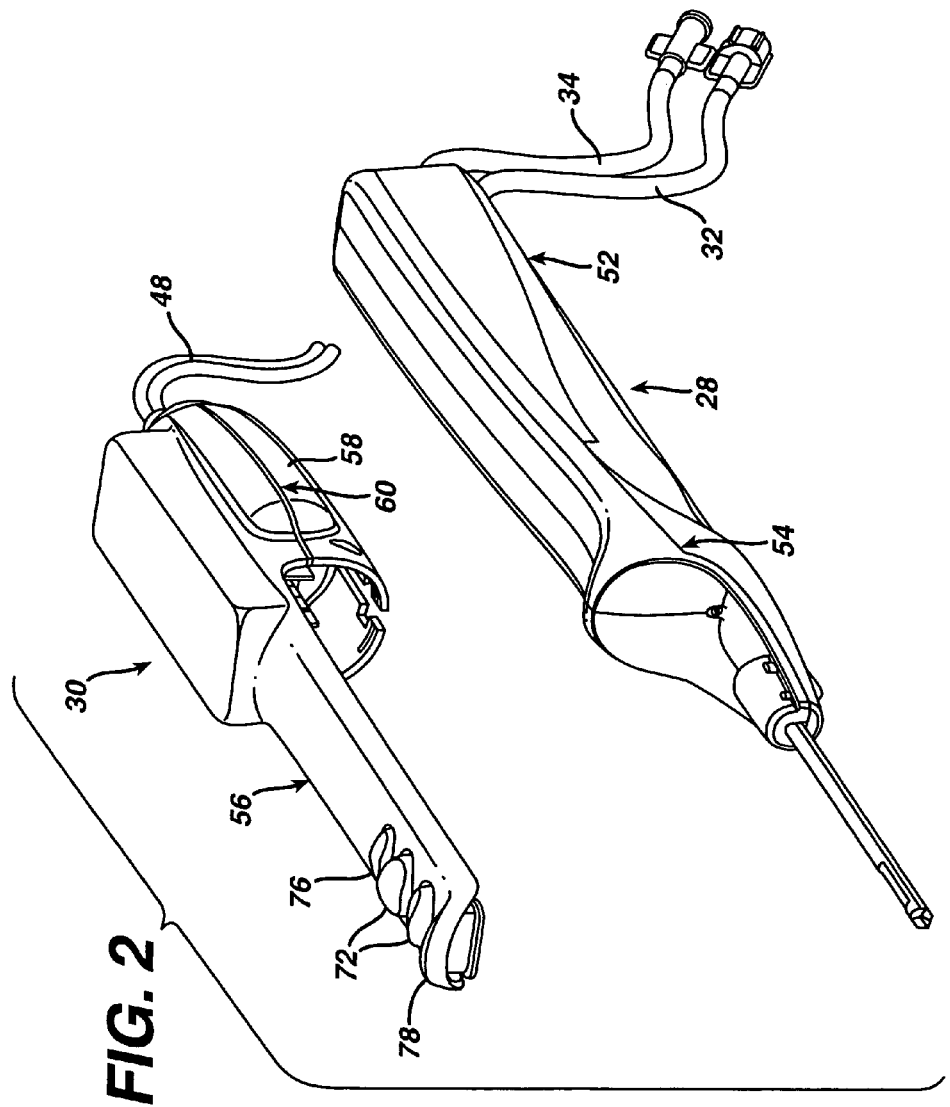
FIG. 2 is an isometric view of the handpiece of FIG. 1, showing a probe assembly prior to attachment to a holster.

FIG. 2 shows probe assembly 28 disconnected from holster 30. Probe assembly 28 includes an upper shell 50 and a lower shell 52 each of which may be injection molded from a rigid, biocompatible plastic, such as a polycarbonate. Upon final assembly of probe assembly 28, upper and lower shells 50, 52 can be joined together along a joining edge 54 by any of a number of methods well known for joining plastic parts, including, without limitation, ultrasonic welding, snap fasteners, interference fit, and adhesive joining. Similarly, holster 30 includes an upper shell 56 and a lower shell 58 which also may be injection molded from a rigid, biocompatible plastic, such as a polycarbonate, and joined together along edge 60 by any suitable method for joining plastic parts.

Figure 3:
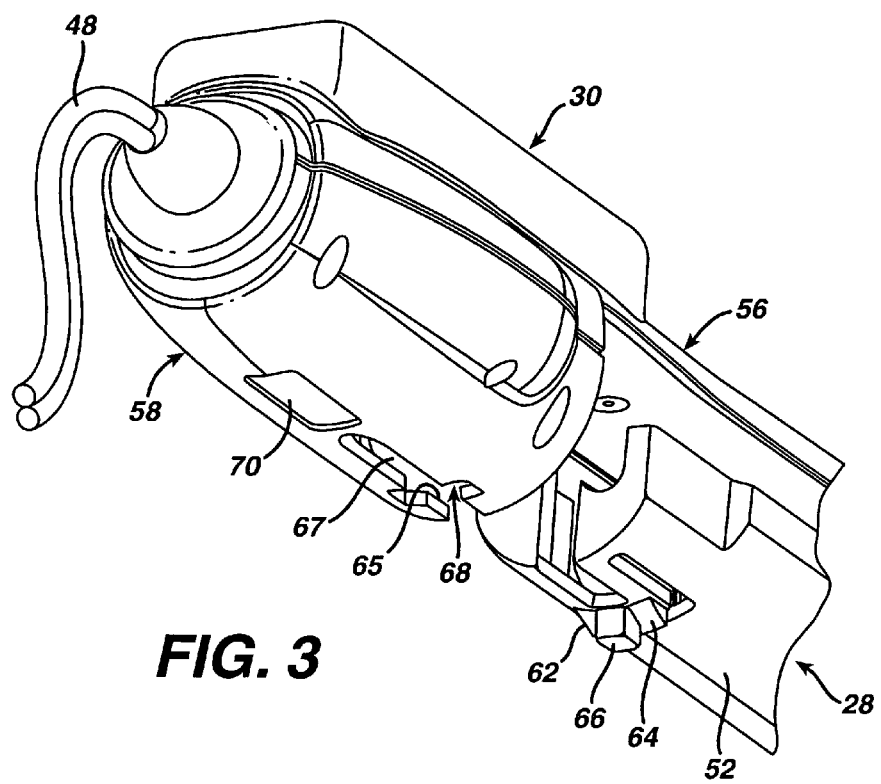
FIG. 3 is an isometric view of the underside of the holster and probe assembly shells, wherein the holster lower shell includes a slot for the removable attachment to a latch on the probe assembly lower shell.
Figure 4:
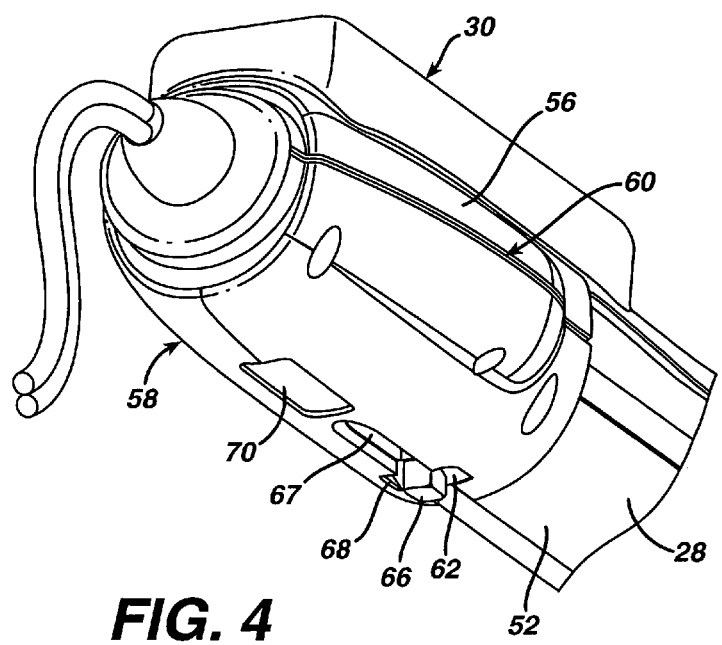
FIG. 4 is an isometric view similar to FIG. 3, illustrating the removable attachment of the holster and probe assembly lower shells.

FIGS. 3 and 4 show the bottom portions of holster 30 and probe lower shell 52. As shown in the figures, a probe latch 62 can be molded into lower probe shell 52 for detachably connecting probe assembly 28 to holster 30. Probe latch 62 is a cantilevered beam and can be deflected downwardly by a force applied to a latch ramp surface 64. Probe latch 62 further comprises a latch projection 66 for insertion into a holster slot 67 as a proximal end of probe assembly 28 is inserted into holster 30. Ramp surface 64 is deflected downwardly by interaction between the surface 64 and an inside surface 65 of holster shell 30. Probe latch 62 retainably snaps into a slot key 68 when probe assembly 28 is fully inserted into holster 30. To remove probe assembly 28 from holster 30, the operator manually depresses projection 66 until ramp surface 64 disengages from slot key 68. Projection 66 may then be pulled axially through slot 67 until the probe assembly 28 and holster 30 are separated.

Returning now to FIGS. 1 and 2, which show that electrical switches are mounted on holster upper shell 56 to enable the operator to use the handpiece 20 with a single hand. These switches can include a two position rocker switch 72 for actuating the motion of the cutter (e.g. forward movement of rocker switch 72 moves the cutter in the forward (distal) direction for tissue sampling and rearward movement of the rocker switch 72 actuates the cutter in the reverse (proximal) direction to position a tissue sample in sample retrieval surface 74), and a vacuum switch 76 for actuating vacuum system 22. One-handed operation allows the operator's other hand to be free, for example, to hold an ultrasonic imaging device. A ridge 78 on the distal end of holster 30 is provided to assist the operator in grasping handpiece 20 and operating switches 72, 76. Probe assembly shells 50, 52 may also be contoured to improve the operator's grip on the instrument during use.

First and second vacuum tubes 32, 34 can be made from a flexible, transparent or translucent material, such as silicon tubing, PVC tubing or polyethylene tubing. This enables visualization of the material flowing through the tubes 32, 34. As shown in FIGS. 3 and 4, one or more slots such as, for example, that indicated by numeral 70, can be provided in holster shell 58 to provide clearance for first and second vacuum tubes 32, 34. An open area at the distal end of probe assembly 28 allows access to sample retrieval surface 74. The operator or an assistant can retrieve a tissue sample from surface 74.

Figure 5:
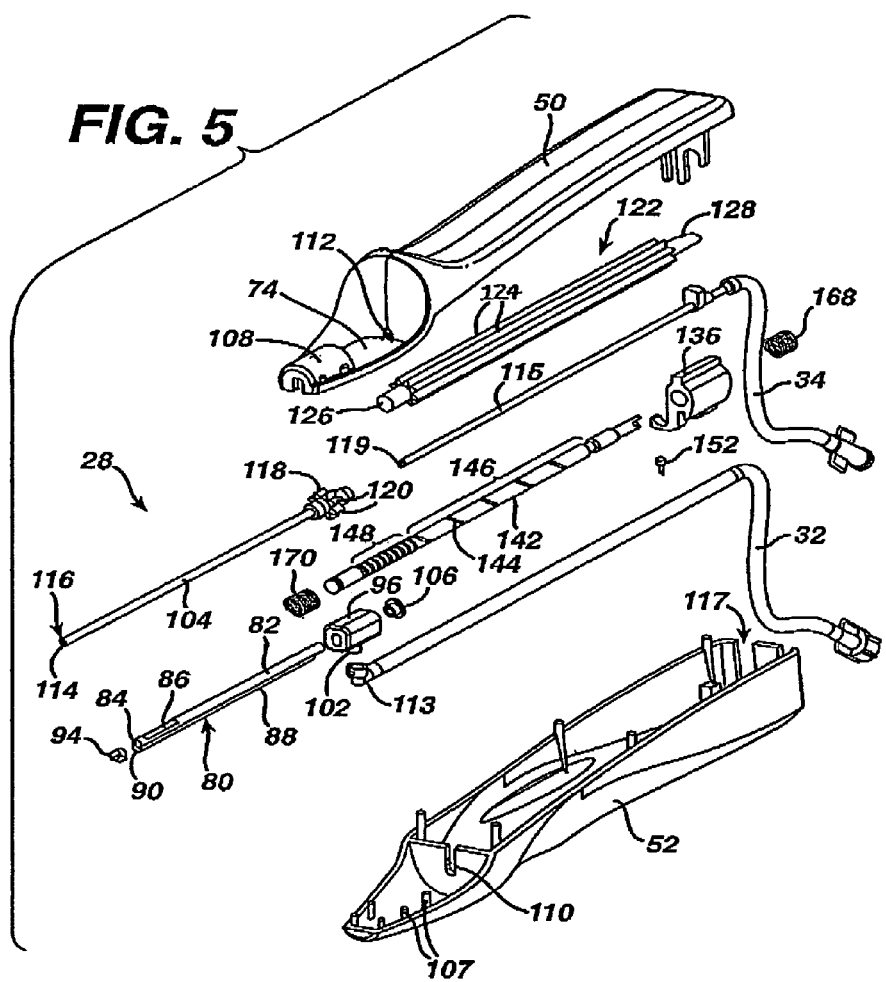
FIG. 5 is an exploded isometric view of the probe assembly illustrated in FIG. 2.
Figure 6:
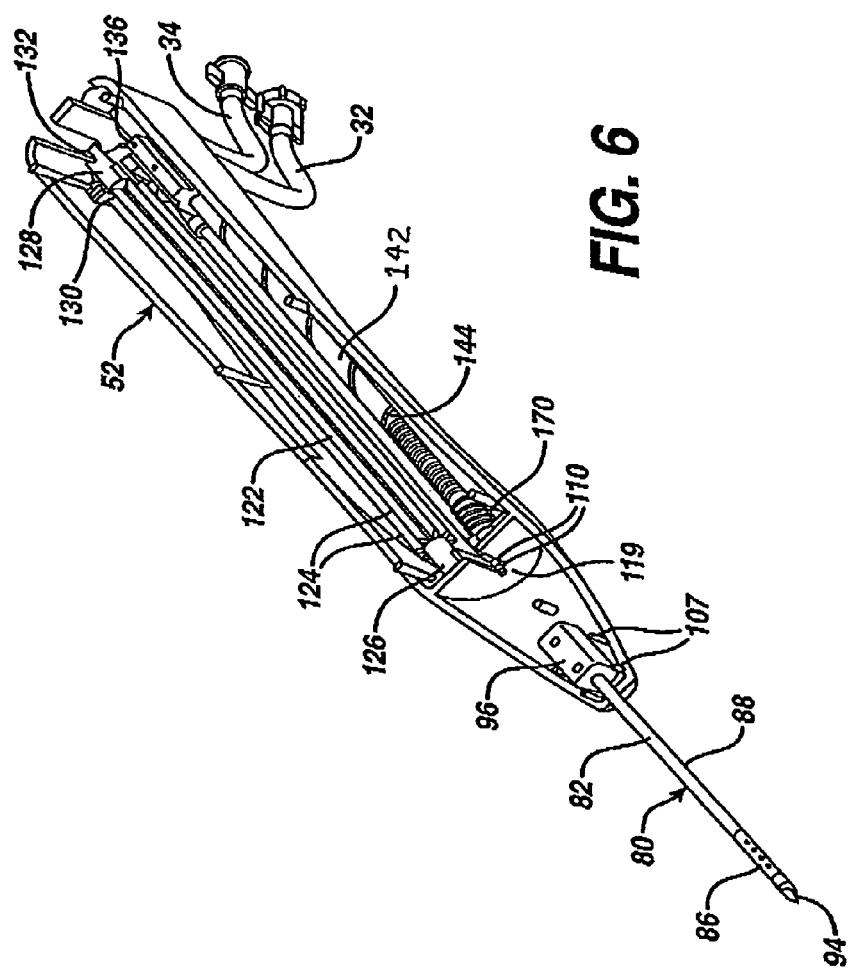
FIG. 6 is an isometric view of the probe assembly of FIG. 2, with the upper shell removed to reveal the internal components.

FIG. 5 provides an exploded isometric view of probe assembly 28. A biopsy needle, including a piercer 80 is located at a distal end of probe assembly 28 for insertion into the surgical patient's skin to obtain a tissue sample. Piercer 80 comprises a cannula having an elongated, metallic piercer tube 82 and an associated lumen 84 extending along the axial length of the tube. Adjacent the distal end of piercer tube 82 is a lateral tissue receiving port 86 for receiving the tissue to be extracted from the surgical patient. Joined alongside piercer tube 82 is an elongated vacuum tube 88 having a vacuum lumen 90. Piercer tube 82 can be formed of any suitable material, including metal or plastic As shown in FIG. 6, piercer lumen 84 is in fluid communication with vacuum lumen 90 via a plurality of vacuum holes 92 located in the bottom of the tissue aperature defined by port 86. These vacuum holes 92 are small enough to remove fluids, but not large enough to allow excised tissue portions to be removed through first vacuum tube 32, which is fluidly connected to vacuum lumen 90 of vacuum tube 88. A sharpened tip of piercer 80 can be formed by a separate piercing endpiece 94 attached to the distal end of the piercer. Endpiece 94 can have a two-sided, flat-shaped point, or other shapes suitable for penetrating the tissue of a surgical patient.

The proximal end of piercer 80 is attached to a union sleeve 96 having a longitudinal bore therethrough, and a transverse opening 102 into a widened center portion of the bore. An elongated, metallic, tubular cutter 104 is axially aligned within the longitudinal bore of union sleeve 96 and piercer lumen 84 of piercer 80 so that the cutter may slide easily in both the distal and proximal directions. A cutter guide 106 is disposed in the proximal end of union sleeve 96. Cutter guide 106 can be in the form of a metallic funnel-shaped guide that ensures proper alignment between cutter 104 and union sleeve 96. Union sleeve 96 and cutter guide 106 are supported between probe upper and lower shells 50, 52 by integrally-formed support ribs 107 extending from lower shell 52, and an integrally-formed housing 108 at the distal end of upper shell 50. These integrally-formed supports 107, 108, along with a slot 110 and opening 112 formed in probe shells 50, 52, ensure proper alignment between the cutter 104 and union sleeve 96 so that the cutter may be translated easily in both the distal and proximal directions. The distal end of first vacuum tube 32 is attached to a polymeric vacuum fitting 113 that inserts tightly into transverse opening 102 of union sleeve 96. Opening 102 is in fluid communication with lumen 90, and allows the communication of fluids in piercer lumen 84 to a vacuum reservoir in vacuum system 22 via vacuum holes 92.

A cutter lumen 114 extends through substantially the entire length of cutter 104. An elongated, hollow, tubular tissue remover 115 can be disposed coaxially within cutter lumen 114, such that cutter 104 may translate along a length of the remover 115. Tissue remover 115 may be metallic or non metallic. Second vacuum line 34 can be fluidly attached to the proximal end of tissue remover 115 to provide vacuum to the cutter lumen 114 via a central passageway extending through the tissue remover 115. Second vacuum tube 34 exits lower shell 52 alongside the first vacuum tube out an opening 117. A strainer 119 is attached to the distal end of tissue remover 115 to prevent fragmented tissue pieces from passing through the remover and into vacuum system 22.

The tissue remover 115 can be held stationary with respect to the lower shell 52 and can be supported by a pair of proximal supports (not shown) on the inside of probe lower shell 52. Second vacuum line 34 provides vacuum through cutter lumen 114 via the hollow remover 115, which vacuum can be used to assist in drawing tissue into tissue receiving port 86 when the distal end of cutter 104 is positioned proximal of the port.

The distal end of cutter 104 is sharpened to form a cutter blade 116 for cutting tissue held against the blade as cutter 104 is rotated. The proximal end of cutter 104 is attached inside an axial bore of a cutter gear 118. Cutter gear 118 may be metallic or polymeric, and includes a plurality of cutter gear teeth 120. Each of the gear teeth 120 has a typical spur gear tooth configuration as is well known in the art.

Referring to FIGS. 5 and 6, cutter gear 118 is driven by an elongated rotary drive shaft 122 having a plurality of drive gear teeth 124 designed to mesh with cutter gear teeth 120. In this embodiment, drive gear teeth 124 extend approximately the entire length of drive shaft 122 and engage cutter gear teeth 120 throughout the translation of cutter 104. Drive gear teeth 124 are in continual engagement with cutter gear teeth 120 to rotate cutter 104 whenever drive shaft 122 is rotatably driven. As will be described in more detail below, drive shaft 122 rotates cutter 104 as the cutter advances distally through tissue receiving port 86 for the cutting of tissue. Drive shaft 122 may be injection molded from a rigid engineering plastic such as liquid crystal polymer material or, alternatively, could be manufactured from a metallic or non-metallic material. Drive shaft 122 could also be extruded from aluminum or machined from a metallic material.

Figure 7:
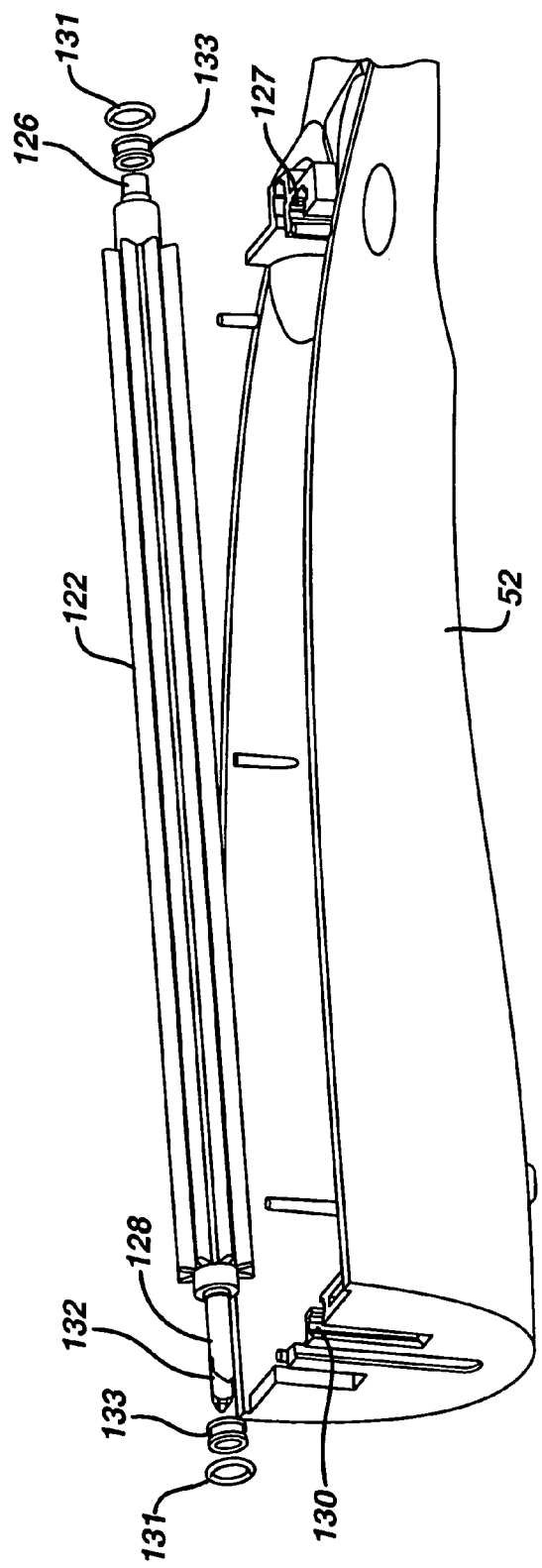
FIG. 7 is an exploded view of the rotary drive shaft and lower probe assembly shell.

As shown in FIG. 7, drive shaft 122 includes a first axial end 126 extending distally from the shaft. Axial end 126 is supported for rotation within probe lower shell 52 by a drive shaft interface 127 molded on the inside of the probe shell. Similarly, a second axial end 128 extends proximally from rotary drive shaft 122 and is supported in a second interface 130 also molded on the inside of probe lower shell 52. An O-ring 131 and bushing 133 may be provided on each axial end 126, 128 so as to sit within interfaces 127, 130 when rotary drive shaft 122 is mounted in probe shell 52. Bushing 133 reduces friction at the drive shaft interfaces 127, 130, while O-ring 131 isolates vibrations in rotary drive shaft 122 from the rest of probe assembly 28. Bushing 133 could also be used without O-ring 131 at interfaces 127, 130. A drive slot 132 is formed in axial end 128. Drive slot 132 interfaces with a corresponding drive slot formed in a motor drive shaft 134, or other rotational drive input for providing rotation of the drive shaft, as will be described further below.

Figure 8:
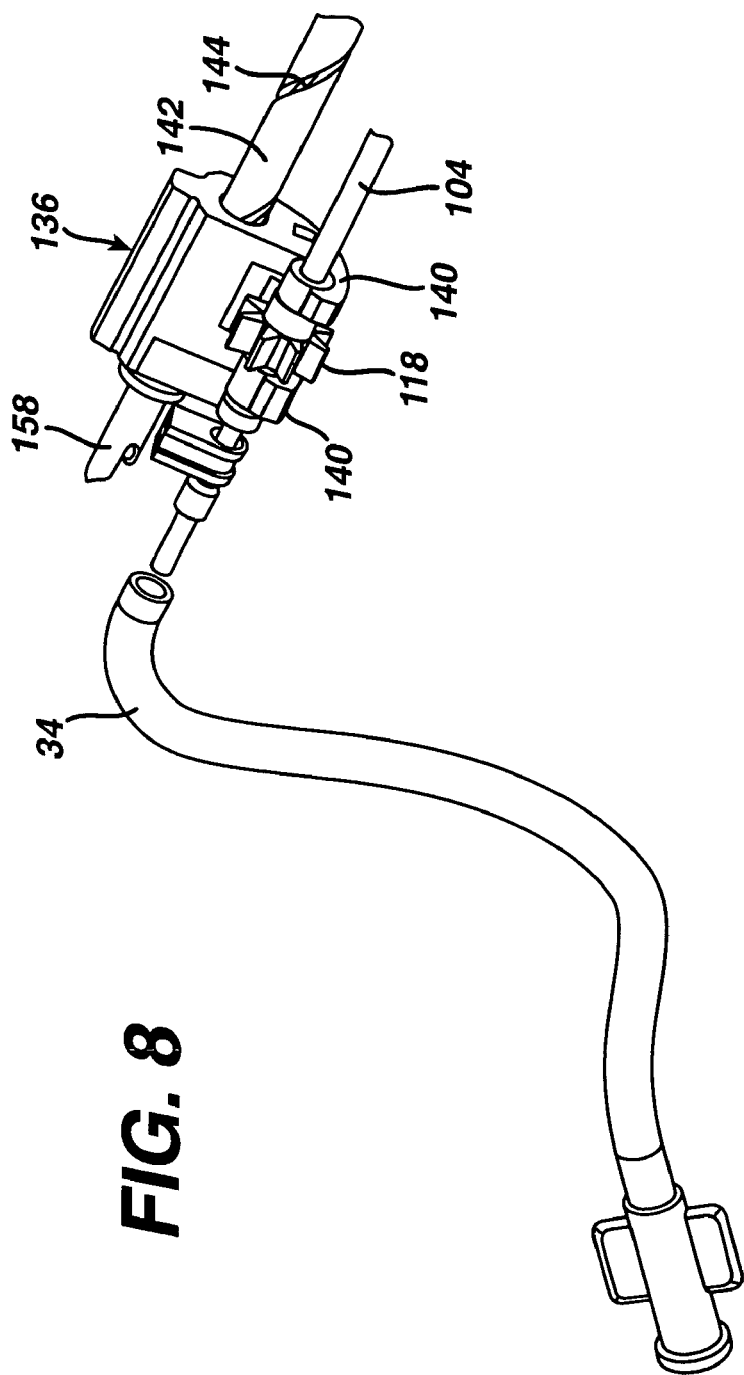
FIG. 8 is a partial isometric view of the translation shaft assembly illustrating the cam track and cam nut.
Figure 9:
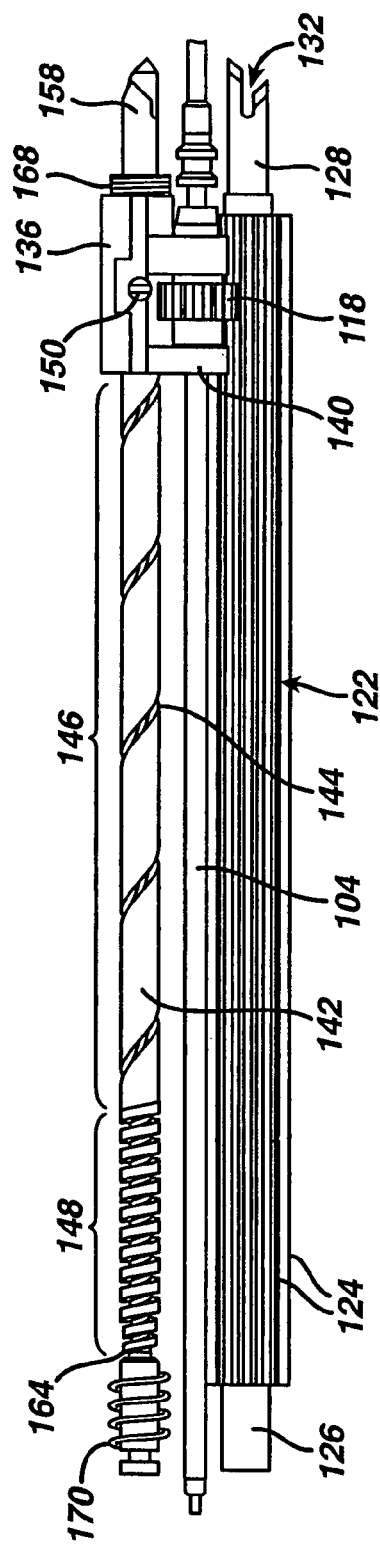
FIG. 9 is a top view of the cutter rotation and translation shaft assemblies.

Referring now to FIGS. 8 and 9, a cam nut 136 is provided in probe assembly 28 to hold cutter gear 118 and carry the cutter gear and attached cutter 104 during translation in both the distal and proximal directions. Cam nut 136 is preferably molded from a rigid polymer and has a cylindrically shaped bore 138 extending axially therethrough. A pair of J-shaped hook extensions 140 extend from one side of cam nut 136. Hook extensions 140 rotatably support cutter 104 on either side of cutter gear 118 to provide proximal and distal translation of gear 118 and cutter 104 during proximal and distal translation of cam nut 136. Hook extensions 140 align cutter 104 and cutter gear 118 in the proper orientation for cutter gear teeth 120 to mesh with drive gear teeth 124.

Cam nut 136 is supported on shaft 142 for translational movement along translation shaft 142. Shaft 142 extends through cam nut bore 138 in parallel with cutter 104 and rotary drive shaft 122. Translation shaft 142 may be made from aluminum or another similar material, and includes a path, such as a path in the form of lead screw thread groove 144 which can be machined or otherwise formed in the outer circumference of the shaft 142. The thread groove 144 can be generally helical. The pitch of lead screw thread groove 144 may vary between the proximal and distal ends of translation shaft 142. In the embodiment described herein, the lead screw pitch varies from a coarser or more widely spaced pitch at the proximal portion of the shaft, to a finer, more closely spaced pitch at the distal portion of the shaft. The particular pitch width of thread groove 144, as well as the ratio of wide to narrow pitch width along the length of the translation shaft, will vary in the present invention depending upon the desired operation of cutter 104.

In the figures, translation shaft 142 is shown with a right hand thread so that clockwise rotation (looking from the proximal to the distal direction) causes cam nut 136 to translate along shaft 142 in the proximal direction, while the reverse rotation of shaft 142 causes cam nut 136 to move in the distal direction. However, the thread direction could also be reversed, with the particular direction of the screw thread depending upon the application and rotary drive input.

Figure 10A:
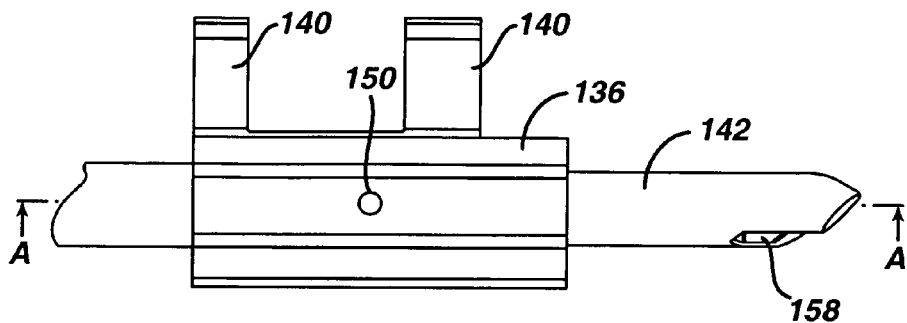
FIG. 10A is a top view of the cam nut follower and translation shaft.
Figure 10B:
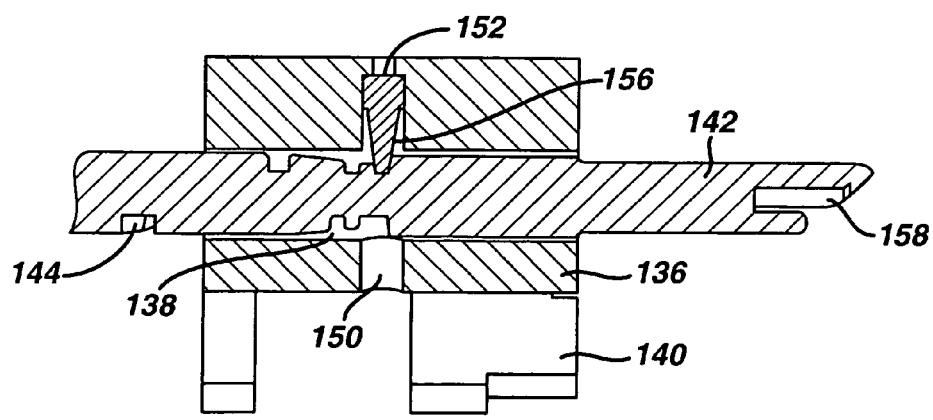
FIG. 10B is a section view taken along section A—A in FIG. 10A.

As shown in greater detail in FIGS. 10A and 10B, cam nut 136 is molded, machined, or otherwise formed to include a receiver hole 150 extending perpendicular to bore 138. A cam follower pin 152 is positioned within receiver hole 150 such that a portion of the pin extends beyond cam nut 136 and into lead screw thread groove 144 of translation shaft 142 as the thread passes through bore 138. Lead screw thread groove 144 forms a path in which to guide cam follower pin 152 about the surface of translation shaft 142 as the shaft is rotated. Cam follower pin 152 can be a metallic, machined pin that is assembled as part of cam nut 136 to create the interface between the cam nut 136 and translation shaft 142. In the embodiment shown, cam follower pin 152 is assembled with an interference fit in cam nut receiver hole 150. Alternatively, pin 152 could be inserted by other methods, such as by insert molding or with screw threads. In yet another embodiment, pin 152 can be supported on cam nut 136 so as to be able to move radially and so "float" in thread groove 144.

As shown in FIG. 10B, cam follower pin 152 sits within cam receiver hole 150 and can have a tapered or otherwised shaped tip, as indicated by angled surface 156, that is shaped to match the profile of cam path 144. Cam path 144 can have a tapered profile. The angled surface 156 allows cam follower pin 152 to freely slide within the tapered pathway formed by lead screw thread 144, and adapt easily to the changing pitch of the thread and/or width of the thread 144.

Returning to FIGS. 8 and 9, a slot 158 is provided in the proximal end of translation shaft 142 for attaching the shaft to a drive motor shaft, such as shaft 160 shown in FIG. 15. Motor shaft 160 provides rotation of translation shaft 142 through mating shaft ends 158, 162. As translation shaft 142 rotates, cam nut 136 follows the variable pitch cam path 144 due to the interface between the path and cam follower pin 152. Accordingly, cam nut 136 translates along the length of shaft 142 as shaft 142 rotates. As cam nut 136 is translated distally by rotation of translation shaft 142, cutter gear 118 is pushed forward (distally) by hook extensions 140. Cutter gear 118 is rigidly attached to cutter 104 to move the cutter in the same direction and at the same speed as the translation of cam nut 136. As translation shaft 142 rotates within cam nut 136, cylindrically shaped bore 138 serves as a bushing to stabilize the cam nut as it traverses translation shaft 142.

During operation of the biopsy instrument of the present invention, cutter 104 translates in either direction between a fully retracted position just proximal to sample retrieval surface 74 and a fully deployed position just distal to tissue receiving port 86. In the embodiment shown, the cutter 104 can translate a distance of about six inches from the fully retracted position to the fully deployed position. There are intermediate positions along the length of the cutter translation which can be identified. When the distal end 116 of cutter 104 reaches each of these positions, adjustments to either the cutter rotational speed (sometimes referred to simply as rotation speed) or the cutter translational speed (sometimes referred to simply as translation speed), or both, may be made, if desired.

For the embodiment of the biopsy device described herein, four positions along the length of the cutter translation may be identified. At each of these positions, adjustments may be made to the cutter rotational and/or translational speed. These speed variations may be accomplished in different manners within the biopsy instrument either mechanically or through motor speed variation. To facilitate description of the cutter positions, they are to be understood as actually the positions of cutter blade 116 on the distal end of cutter 104. These four cutter positions are the following: a first position where cutter 104 is just proximal to sample retrieval surface 74; a second position where cutter 104 is just distal to sample retrieval surface 74; a third position where cutter 104 is just proximal to tissue receiving port 86; and a fourth position where cutter 104 is just distal to port 86. These four positions are sometimes referred to as position one, position two, position three, and position four. These four cutter positions are given by way of example only, and numerous other cutter positions may be used in the present invention for signaling adjustments to cutter rotational speed an/or translational speed without departing from the scope of the invention.

In the embodiment shown in FIGS. 5, 6 and 9, as cutter 104 translates from position one to position two along the translational length, cam follower pin 152 traverses the coarser pitched portion 146 of groove 144, thereby translating at a more rapid speed for each rotation of translation shaft 142. As cutter 104 moves from position two to position three, cam groove 144 transitions from a coarser pitch width to a finer pitch width, thereby slowing the translation speed of cutter 104 for each rotation of shaft 142. As cutter 104 approaches position three, drive shaft 122 begins rotating to correspondingly rotate the cutter. Accordingly, cutter 104 begins to rotate when cam follower pin 152 begins traversing the slower, fine pitch portion 148 of cam groove 144. The translation speed of cutter 104 is slowed in the finer pitch portion 148 to advance the rotating cutter 104 more slowly through tissue receiving port 86 during the cutting of tissue. During translation through tissue receiving port 86 (between positions three and four), cutter 104 is rotated by drive shaft 122 at the desired tissue cutting speed.

The pitch width of cam groove 144 determines the linear distance traveled by cam nut 136 for each 360° rotation of translation shaft 142. The wider the pitch width of thread groove 144, the greater the linear distance traveled by cutter 104 for each 360° rotation of shaft 142. Accordingly, the linear speed of cutter 104 may be varied as a function of the location of cam nut 136 on translation shaft 142. The pitch of thread groove 144 can be selected to provide a desired ratio of cutter translational speed to rotational speed of translation shaft 142. Thread groove 144 can function as a variable pitch cam path.

Figure 11:
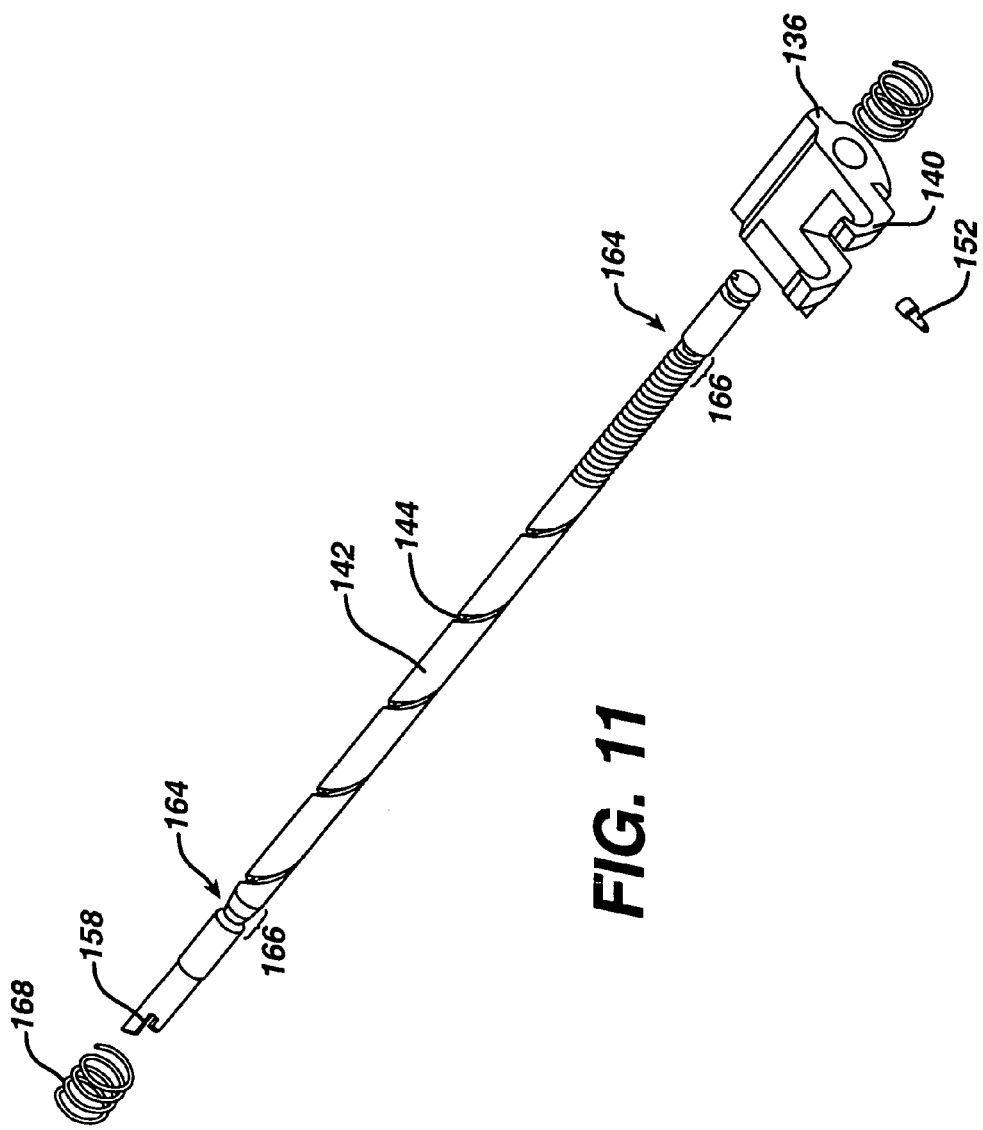
FIG. 11 is an exploded isometric view of the translation shaft assembly.

FIGS. 9 and 11 illustrate the full extent of translation shaft 142 as well as the variable pitch thread groove 144. As shown in these figures, translation shaft 142 may include areas adjacent the proximal and distal ends of the shaft where translation of cutter 104 is prevented regardless of the rotation of shaft 142. In these areas, indicated by numeral 164, lead screw thread groove 144 may have a pitch width of zero, and thereby form a 360° groove about the circumference of the shaft. The 360° groove or no-pitch zone 164 inhibits travel of cam nut 136 along translation shaft 142. As thread groove 144 transitions to no-pitch zone 164, the diameter of translation shaft 142 can be decreased as indicated at 166, and the pitch of thread groove 144 made finer, to slow the translation of the pin 152, and so the cutter 104.

When cam nut 136 enters the no-pitch zone, shaft 142 may continue to rotate but the cam nut is prevented from translating along the shaft due to the retention of cam follower pin 152 within groove 164. When cutter 104 is at its distal most (or proximal most) point of travel, and the rotation direction of shaft 142 is reversed (such as by depressing rocker switch 72), cam follower pin 152 can be urged from no-pitch zone 164 back into engagement with variable pitch thread groove 144. As shown in FIG. 11, a biasing device such as coil springs 168, 170 may be provided adjacent each end of translation shaft 142 for urging cam nut 136 back into engagement with variable pitch thread groove 144 when the translation direction changes upon reversing the direction of rotation of shaft 142. Reducing the outer diameter of the shaft 142 at 166 adjacent the no-pitch zone 164 and making the pitch of the thread groove 144 finer can also be beneficial in reducing noise or vibration of the pin 152 as it rides in groove of the no-pitch zone 164.

Figure 12A:
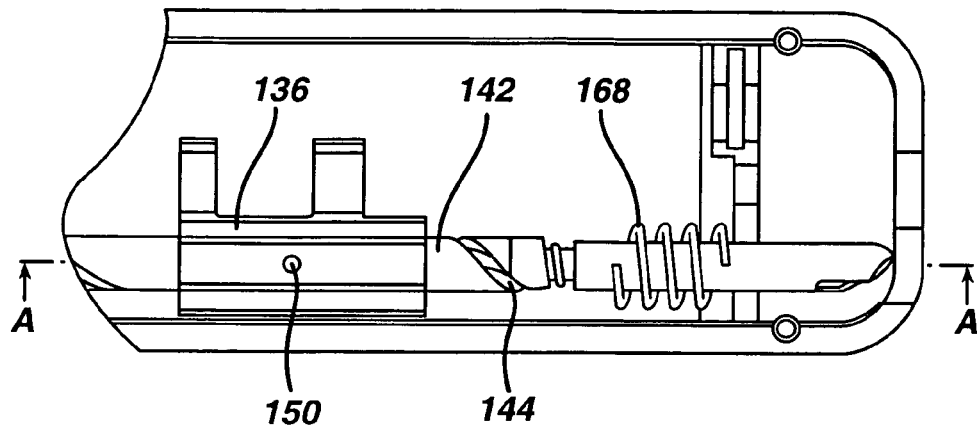
FIG. 12A is a top view of the cam nut adjacent the proximal end of the translation shaft.
Figure 12B:
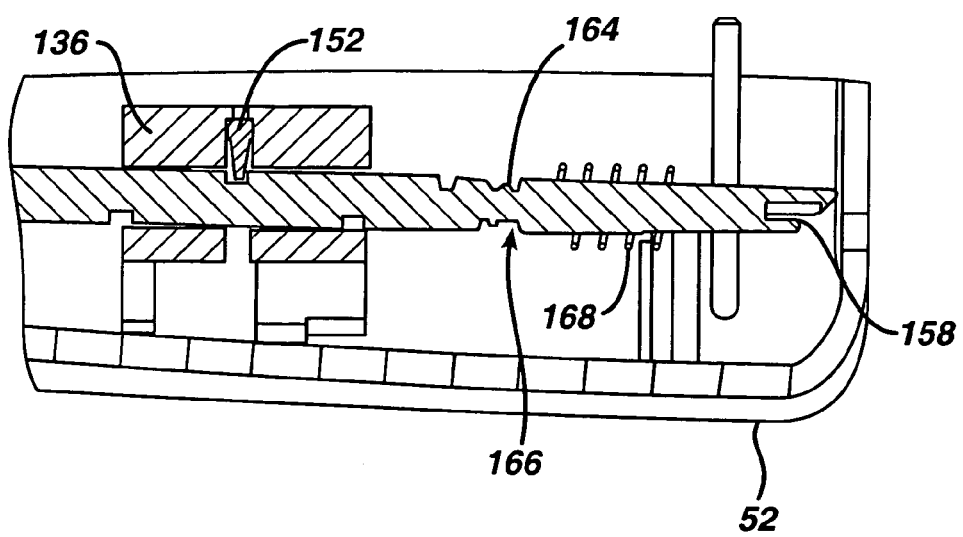
FIG. 12B is a section view taken along section A—A in FIG. 12A.
Figure 13A:
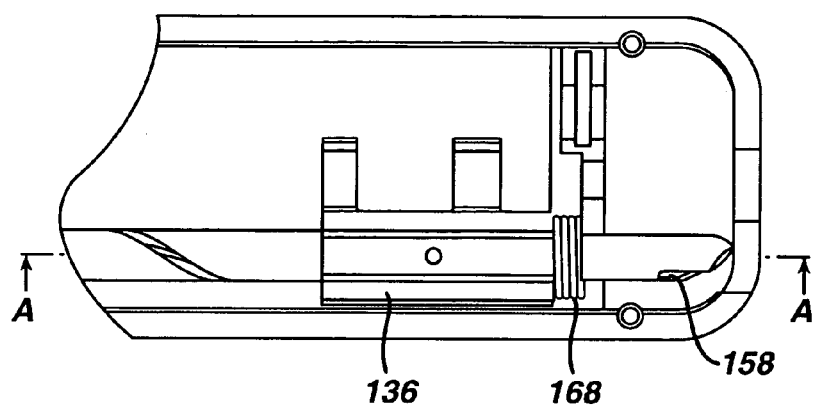
FIG. 13A is a top view of the cam nut at the proximal most position of the translation shaft.
Figure 13B:
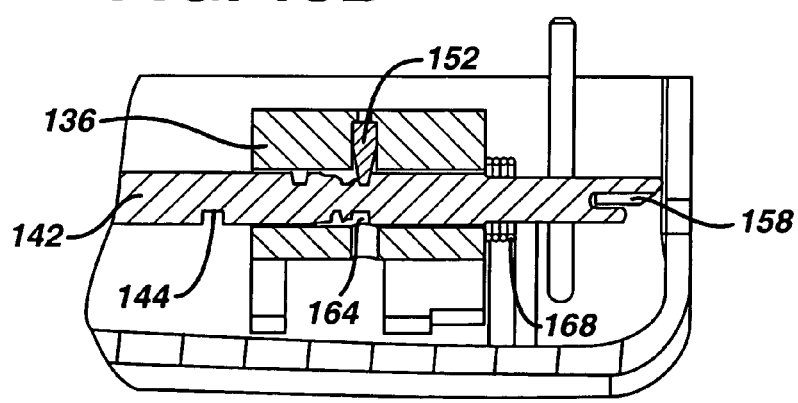
FIG. 13B is a section view taken along section A—A in FIG. 13A.

FIGS. 12A and 12B illustrate no-pitch zone 164 and spring 168 as cam nut 136 translates towards the proximal end of shaft 142. FIGS. 13A and 13B illustrate cam nut 136 after it has translated to its most proximal position (i.e. cutter position one). In this position, cam follower pin 152 engages no-pitch groove 164 and spring 168 is compressed against cam nut 136. Cam nut 136 remains in this position as shaft 142 rotates due to cam follower pin 152 engaging no pitch zone 164. Once the rotation direction of shaft 142 is reversed, such as by changing motor direction, energy stored in spring 168 acts against cam nut 136 to push the cam nut 136 (via cam follower pin 152) out of no-pitch zone 164. Spring 168 pushes cam nut 136 back into engagement with variable pitch path corresponding to thread groove 144 so that the cam nut (and cutter 104) can begin translating in the opposite direction.

The outer diameter of the shaft 142 can be machined or otherwise reduced and the threads (e.g. with tapered walls) of thread groove more closely spaced to provide a finer pitch (more threads per inch). In an alternative embodiment, the thread depth of cam path 144 having tapered thread walls may be varied in order to vary the translation speed of cam follower pin 152. For instance, the depth of cam path 144 may be reduced, while the diameter of shaft 142 remains constant, to enable the screw threads to be placed more closely together on the shaft. The closer spaced threads reduce the linear distance traveled by cutter 104 during each revolution of translation shaft 142.

FIGS. 14A–14C depict three of the four positions of cutter 104 during the operation of the present invention as embodied in the prior FIGS. 1–13. The three positions of cutter 104 are most easily distinguished by observing the relative positions of cam nut 136 (which moves together with cutter 104) and cutting edge 116 on the distal end of cutter 104. FIG. 14A shows a partially cut away top view of probe assembly 28 in which cutter 104 is located in position one. In this position, cutter 104 is in a fully retracted position, with cutting edge 116 positioned proximal of sample retrieval surface 74. Cam nut 136 is positioned at the proximal end of translation shaft 142 with cam follower pin 152 rotating within the no-pitch zone 164 of cam path 144. Spring 168 is compressed against the proximal end of cam nut 136. In the position shown in FIG. 14A, cutter 104 is in a fully retracted position such that port 86 in piercer 80 is open to receive tissue. In this position, a tissue sample may be retrieved from sample retrieval surface 74.

FIG. 14B illustrates cutter 104 advanced to the third position in which cutting edge 116 is immediately proximal of tissue receiving port 86. In this position, cam nut 136 has translated along shaft 142 to a point where cam follower pin 152 is transitioning from wider pitch portion 146 to finer pitch portion 148 of thread groove 144. Likewise, cutter 104 has advanced to an intermediate position in which drive shaft 122 is rotating the cutter via cutter gear teeth 120 and drive gear teeth 124. Cutter blade 116 is located in a position immediately proximal to port 86. Vacuum holes 92 in port 86 are open so that soft tissue adjacent to port 86 can be pulled into the port when first vacuum tube 32 is fluidly connected to vacuum system 22.

FIG. 14C illustrates cutter 104 advanced to the fourth position, in which the cutter is in the most extended position and cutting edge 116 is distal of port 86. In this position, cutter 104 is being rotated at an appropriate cutting speed by rotary drive shaft 122. Tissue pulled into port 86 by the vacuum through holes 92 has been severed by the rotating, advancing cutter blade 116 and stored inside cutter lumen 114. When cutter 104 retracts back to the first position shown in FIG. 14A, tissue remover 115 draws the tissue sample back to sample retrieval surface 74. In FIG. 14C, cam nut 136 is shown in its most distal position, having translated through fine pitch portion 148 of cam path 144. In this position, cam follower pin 152 is engaged in no pitch zone 164 at the distal end of variable pitch cam slot 144. Spring 170 is compressed by cam nut 136 for biasing the cam nut back into engagement with fine pitch portion 148 of cam path 144 once the direction of rotation of translation shaft 142 is reversed, and cutter 104 is retracted back to position one.

Figure 16:
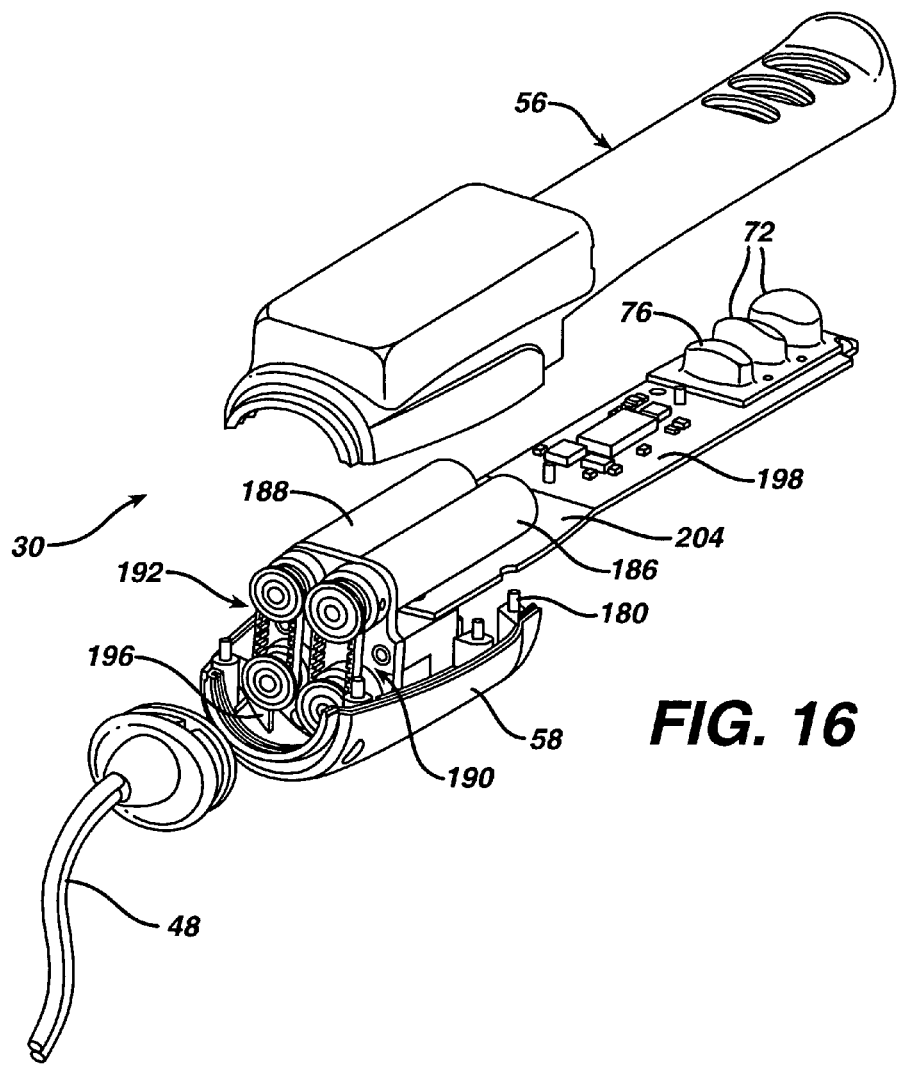
FIG. 16 is a rear isometric view of the holster assembly of FIG. 15, wherein the holster upper shell is detached to reveal the double motor assembly.

FIG. 15 is an exploded isometric view of a first embodiment of holster 30. In this embodiment, holster 30 is an integrally motorized holster in which two motors are supported for rotatably driving shafts 122, 142 in probe assembly 28. As mentioned above, holster 30 includes an upper shell 56 and a lower shell 58 which may be shaped as shown in FIGS. 15 and 16 to accommodate the motors and motor drive shafts enclosed therein. Upon final assembly, shells 56, 58 are joined together by screws 180 fastened into a plurality of alignment holes 182, or attached together by another type of fastener well known in the art.

A pair of motor drive shafts 134, 160 is contained within the proximal enclosed portion of holster 30. The first drive shaft 134 has a distal end 172 shaped to operatively engage slot 132 of rotary drive shaft 122. The second drive shaft 160 has a distal end 162 shaped to operatively engage slot 158 of translation shaft 142. Motor drive shafts 134, 160 extend distally from a gear case 184 for engagement with drive and translation shafts 122, 142 when probe assembly 28 and holster 30 are connected. A first drive motor 186 and second drive motor 188 are mounted above gear case 184. First drive motor 186 provides rotary motion to drive shaft 134 through a gear assembly 190 shown in FIG. 16. The rotary motion produced in drive shaft 134 is transferred through distal end 172 and slot 132 to rotary drive shaft 122 when probe assembly 28 and holster 30 are connected. Likewise, second drive motor 188 provides rotary motion to drive shaft 160 through a second gear assembly 192. The rotary motion of drive shaft 160 is transferred to translation shaft 142 by the engagement between slot 158 and distal shaft end 162. Motors 186 and 188 can be DC graphite brush motors, such as Model 118718 4.5 Watt motors available from Maxon Precision Motors of Sachsein, Switzerland. Motor 186 can be employed with a planetary gearhead Model 118184 available from Maxon, and Motor 188 can be employed with a planetary gearhead Model 110322 available from Maxon.

Figure 17:
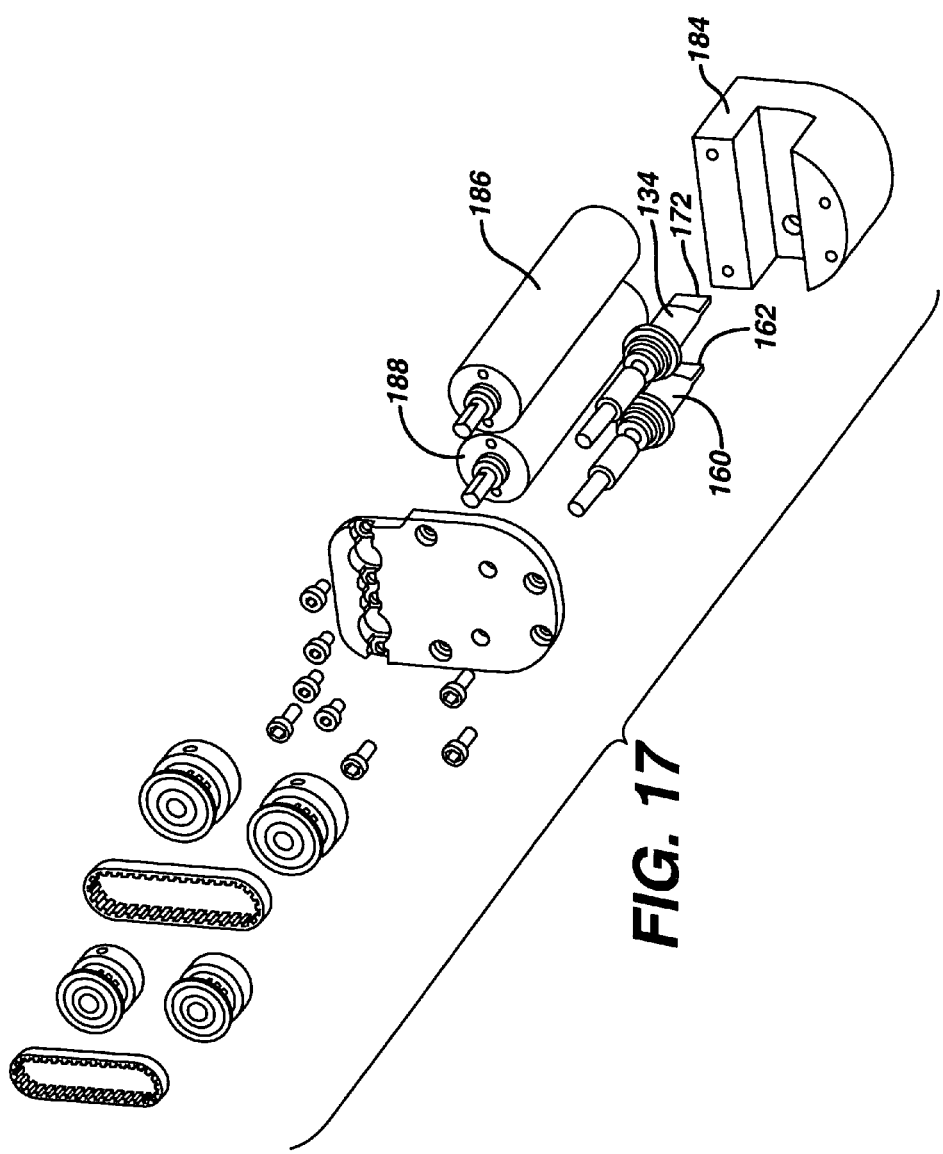
FIG. 17 is an exploded isometric view of the double motor assembly of FIG. 16.

Referring to FIGS. 16 and 17, first and second gear assemblies 190, 192 are positioned at the proximal end of motors 186, 188 and drive shafts 134, 160, and are each comprised of a pair of gears interconnected by a belt. The separate connections between motors 186, 188 and drive shafts 134, 160 enables the drive shafts to be separately driven at different time periods and at different speeds without the need for additional gearing. Further, because individual motors are used to drive shafts 134, 160 the motors may be smaller and less powerful than that required to drive both shafts in combination.

Motors 186 and 188 can be supported in holster 30 in any convenient manner, such as, for example, by one or more supports 196 molded into holster lower shell 58. A switchboard 198 is provided in holster 30 and electrically interfaced with motors 186, 188 in any convenient manner. Switchboard 198 can also interface with various user interface switches such as rocker switch 72 and vacuum switch 76, as well as control cord 48 that provides power and control signals to holster 30 from control unit 24. Switch seals 200 and 202 comprised of a polymeric rubber or other suitable sealing material can be provided between switchboard 198 and adjacent components to prevent fluid from entering holster 30 and affecting switchboard 198. A metal plate 204 can be provided with mounting or connecting features to provide structural support within holster 30 and/or facilitate fastening of the holster to probe assembly 28.

Figure 18:
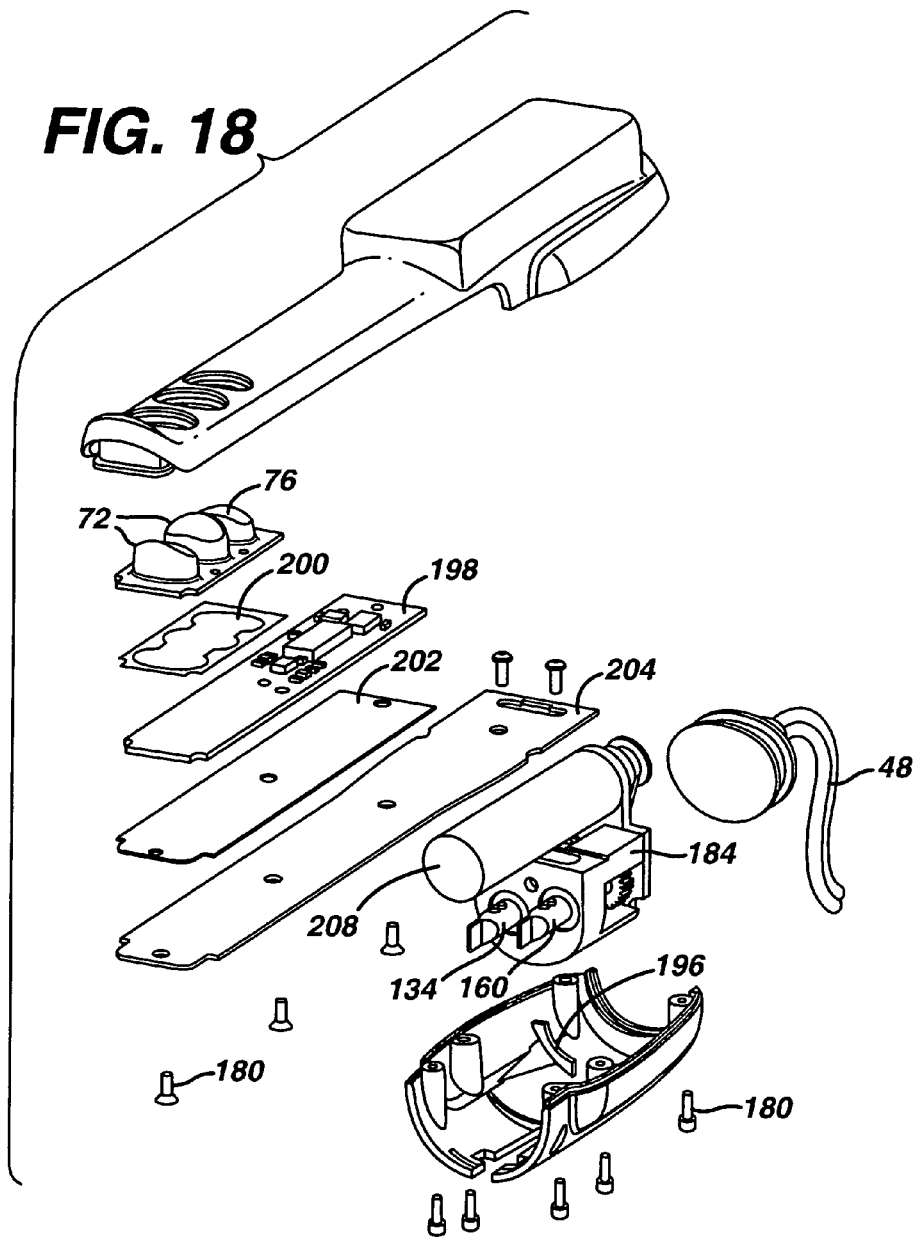
FIG. 18 is an exploded isometric view of the holster depicting a second, single motor embodiment of the present invention.
Figure 19:
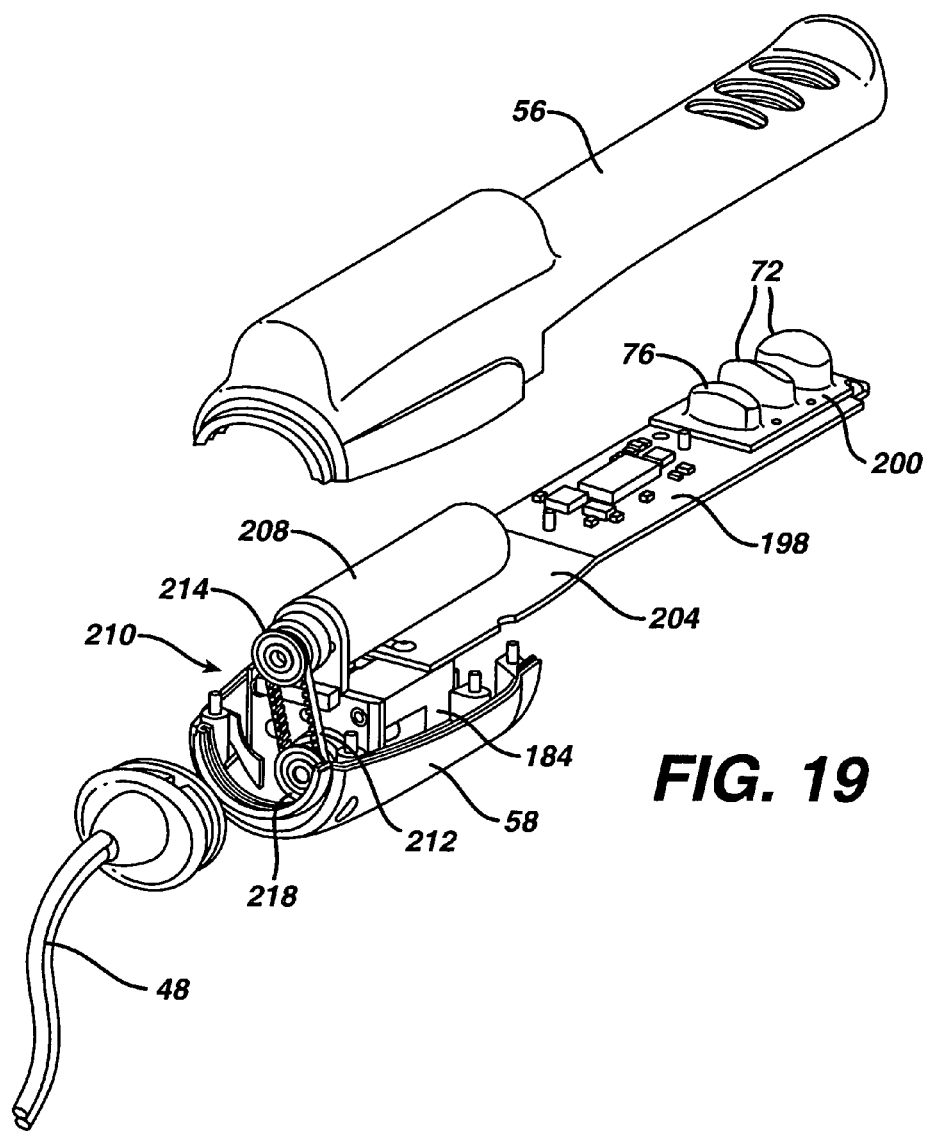
FIG. 19 is a rear isometric view of the holster of FIG. 18, wherein the holster upper shell is detached to reveal the single motor assembly.
Figure 20:
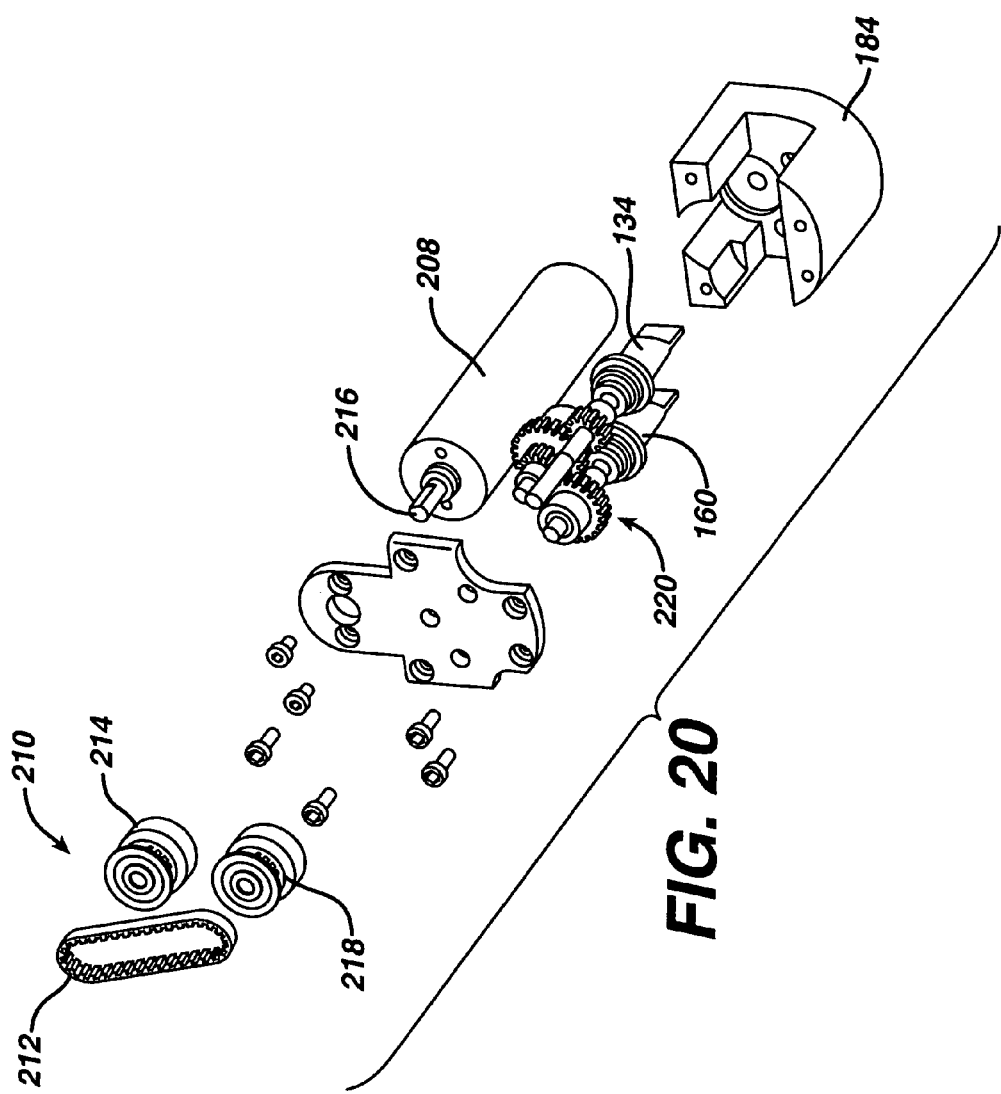
FIG. 20 is an exploded isometric view of the single motor assembly of FIG. 19.

The embodiment shown in FIGS. 15–17 comprises two integral motors mounted above gear case 184 and directly connected to motor drive shafts 134, 160 for separately driving each shaft. In an alternative embodiment, such as shown in FIGS. 18–20, a single integral motor could be used to drive both the rotary drive shaft and the translation shaft through suitable gearing. In this embodiment, the single motor 208 may be mounted above gear case 184 and motor drive shafts 134, 160 in the proximal end of the holster. Motor 208 is operatively connected to drive shafts 134, 160 through a gear assembly 210. FIGS. 19 and 20 provide a rear view of the single motor assembly illustrating the interconnection between motor 208 and gear assembly 210. This interconnection includes a single belt 212 extending between gear 214 of motor shaft 216 and gear 218 of drive shaft 134. As shown in FIG. 20, additional gears 220 are included in gear case 184 for driving translation shaft 160 from the rotation of rotary drive shaft 134. The additional gears 220 provide a gear reduction between the two drive shafts 134, 160 to enable translation drive shaft 160 to rotate at a slower speed than rotary drive shaft 134. Gears 220 could also be configured to enable translation drive shaft 160 to rotate at a faster speed than rotary drive shaft 134, or for the two shafts to rotate at the same speed, depending upon the desired operation of cutter 104. In addition to the two embodiments described above, the present invention could also comprise one or more integral motors positioned at the proximal end of holster 30 behind gear case 184, along the side or bottom portions of the holster, or in a forward end of the holster. In addition, one or more drive motors could be located external of the holster and operatively connected to rotary drive and translation shafts 122, 142 by one or more rotatable shafts. Accordingly, the particular location of the motors in the present invention may be varied depending upon the desired size or weight distribution for the holster.

Figure 21:
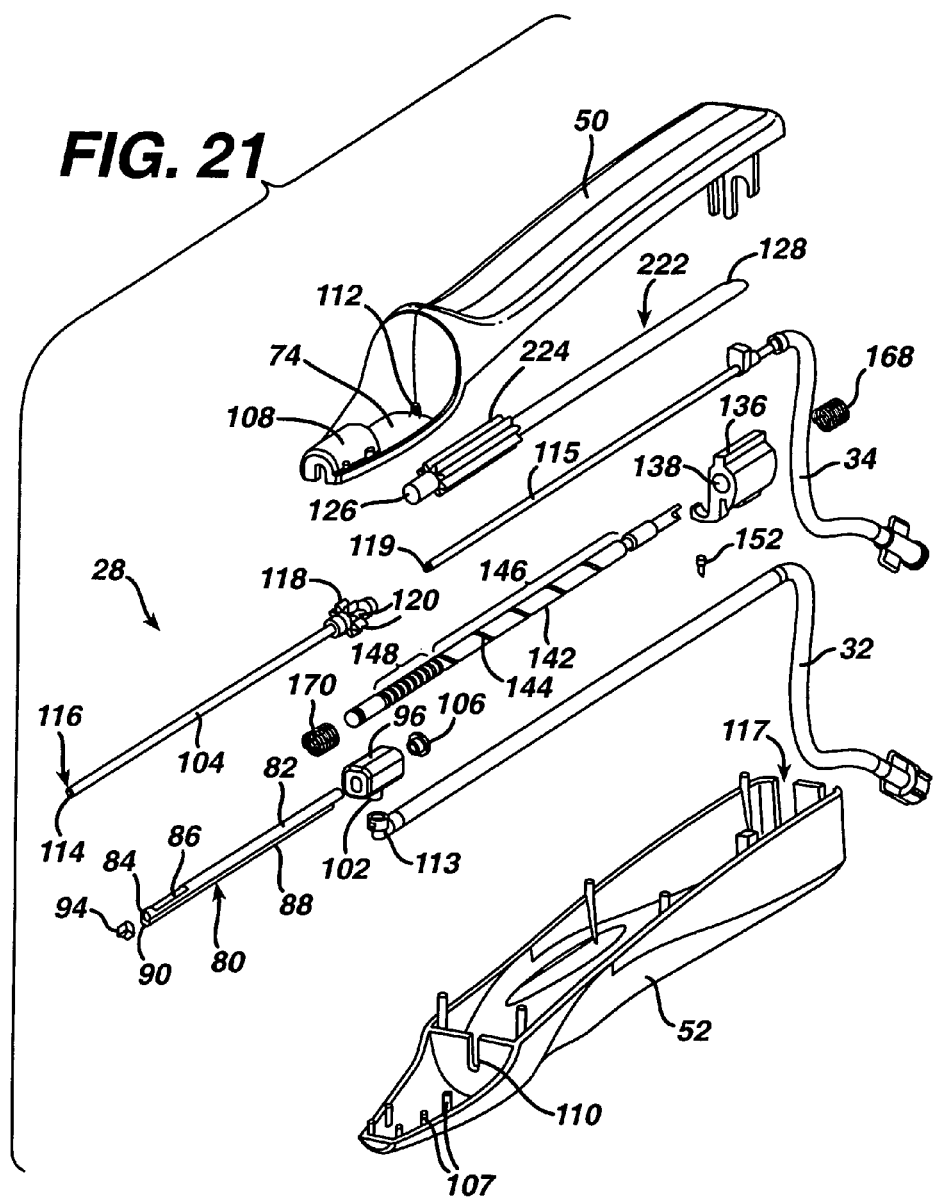
FIG. 21 is an exploded isometric view of a probe assembly for the second, single motor embodiment.
Figure 22:
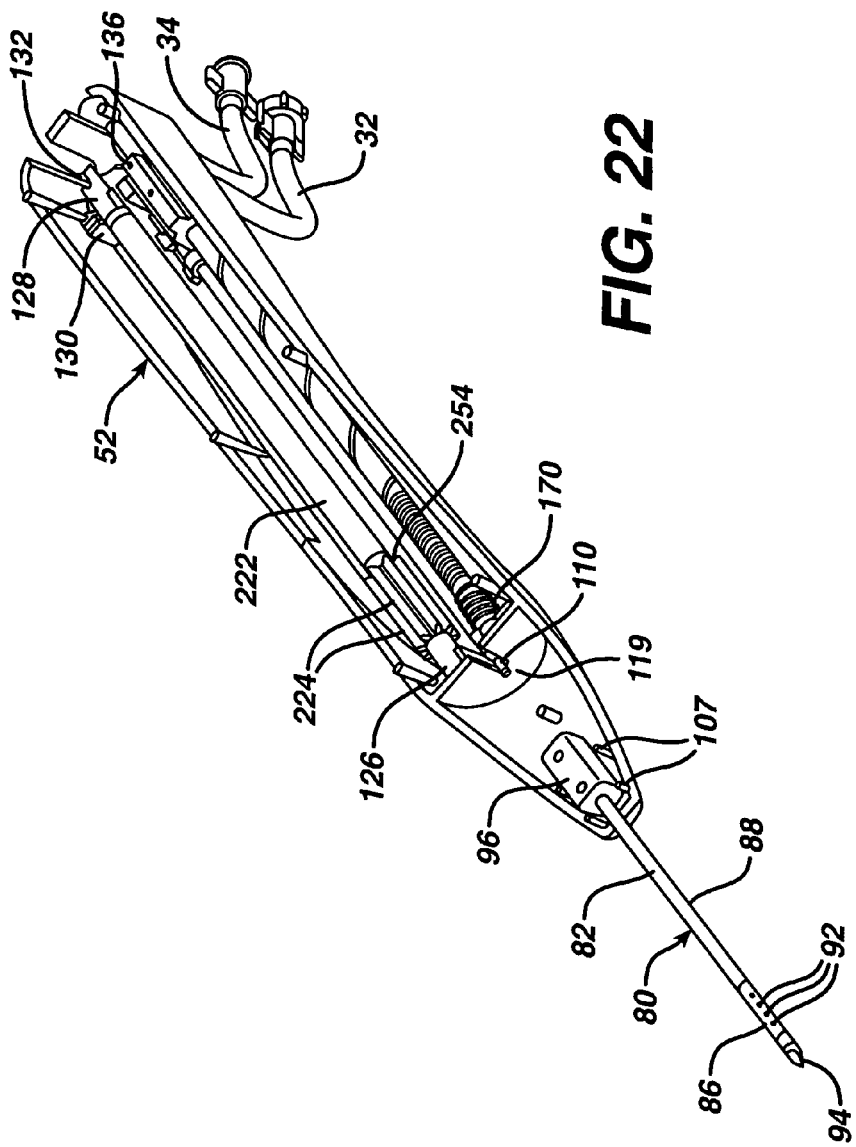
FIG. 22 is an isometric view of the probe assembly of FIG. 21, with the upper shell removed to reveal the internal components.

FIGS. 21 and 22 illustrate probe assembly 28 for the second, single motor embodiment of the invention. In the single motor embodiment, both the rotary drive shaft 134 and translation drive shaft 160 are rotated during the entire operation of the device, since a common motor 208 acting through gears 214, 218 and belt 212 drives the shafts simultaneously. To accommodate the continuous rotation of motor drive shaft 134, the rotary drive shaft 122 of the first embodiment is replaced with a modified drive shaft 222 having drive gear teeth 224 located proximate the distal end of the drive shaft. With gear teeth 224 in this position, cutter gear 118 engages modified drive shaft 222 only after cutter 104 has advanced distally to a position just proximal of tissue receiving port 86. When cutter gear 118 engages drive gear teeth 224, the gear teeth 120, 224 mesh and cutter 104 is rotated by drive shaft 222. Drive gear teeth 224 may include a lead-in ramp 254 molded in the proximal end of drive gear teeth 224. Ramp 254 transitions gear teeth 120 into engagement with drive gear teeth 224 to provide a smooth meshing of the gears. Drive shaft 222 is modified in this manner for the single motor embodiment so that cutter 104 rotates only during the tissue-cutting phase of the cutter advance.

Figure 23:
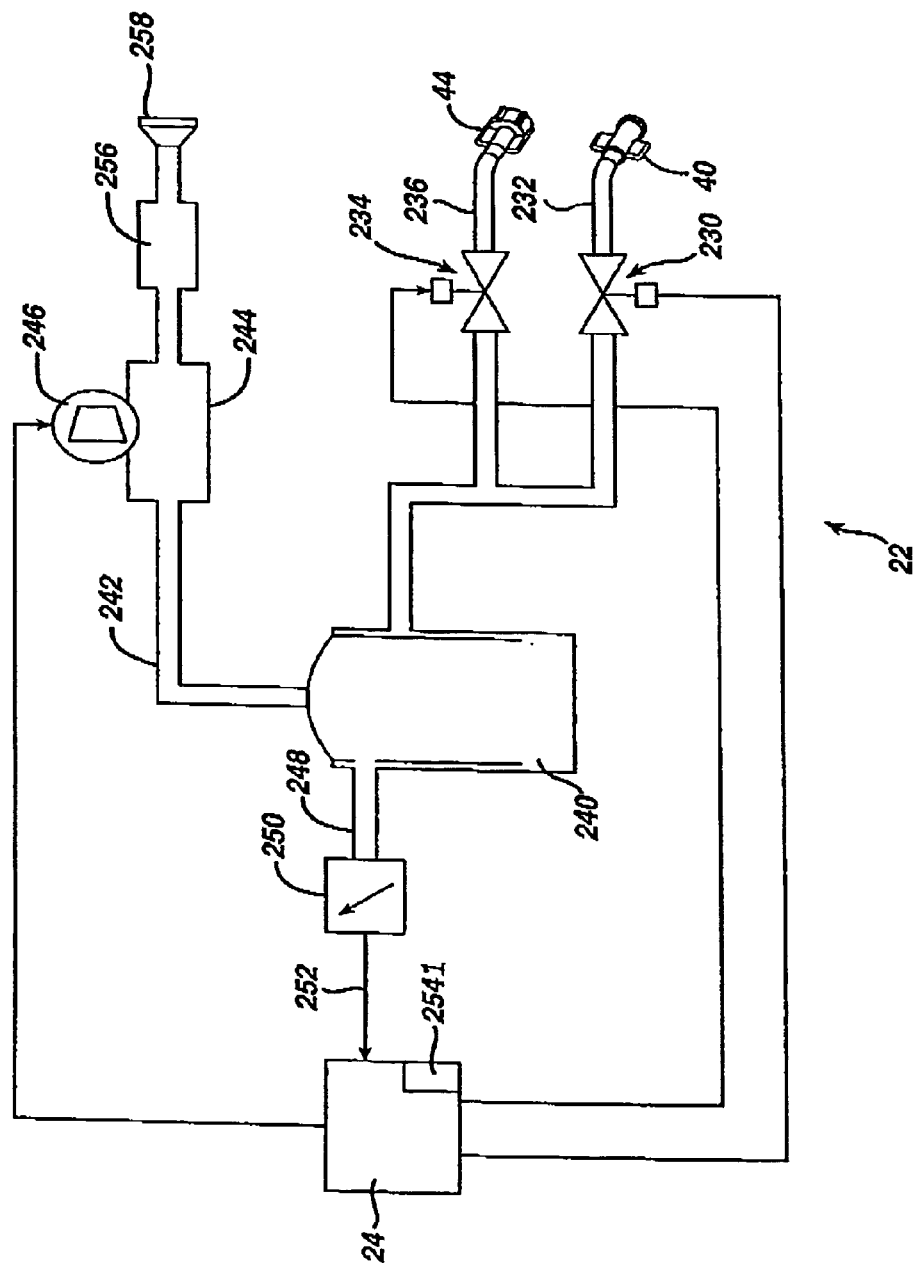
FIG. 23 is a schematic diagram of a vacuum system in accordance with the present invention.

FIG. 23 shows vacuum system 22 in greater detail. As shown in FIG. 23, vacuum system 22 comprises a first valve 230 connected by a vacuum tube 232 to first connecter 40. A second valve 234 is connected by a second vacuum tube 236 to second connector 44. Valves 230, 234 control the supply of vacuum to lateral vacuum line 32 and axial vacuum line 34 respectively. Valves 230, 234 include solenoids that are controlled by signals from control unit 24 to open and close vacuum tubes 232, 236 during operation of biopsy instrument 20. Each of the vacuum tubes 232, 236 may be separately opened and closed at different intervals during an operation cycle. Vacuum lines 232, 236 extend from valves 230, 234 to a fluid reservoir, such as vacuum reservoir 240. A main vacuum line 242 attaches reservoir 240 to a vacuum pump and chamber, indicated by numeral 244, which is driven by a motor 246. Vacuum pump 244 may be of various types, such as, for example, a piston, diaphragm, rotary or rotary vane pump. Motor 246 is preferably of a type operable at variable speeds, such as, for example, a brushless direct current motor. The speed of the motor can be controlled based on a pressure sensed in a fluid reservoir, such as a vacuum level in the vacuum reservoir 240. The speed of the motor may also be controlled based on upon an anticipated need for vacuum during an operation cycle, such as based on a schedule of desired cutter position.

A muffler and baffling system 256 and exhaust port 258 extend from vacuum chamber 244 to reduce noise and vent the system. An additional vacuum tube 248 extends from vacuum reservoir 240 to a vacuum pressure sensor 250. Sensor 250 monitors the vacuum pressure in reservoir 240 and periodically transmits a pressure signal 252 to control system 24. Control system 24 includes a printed circuit board (PCB) with a microprocessor or microcontroller 2541 for controlling motor 246 in relation to the pressure signal 252 from sensor 250.

In one embodiment, microcontroller 2541 maintains a consistent, desired vacuum pressure in reservoir 240 by adjusting the speed of motor 246 in relation to pressure signal 252 from sensor 250. The motor speed may be adjusted by altering the current, voltage or torque of the motor to vary the vacuum pump speed, and/or turn the vacuum pump on and off. In one embodiment, while the pressure within reservoir 240 is at a desired preset level, microcontroller 2541 idles motor 246 so that vacuum pump 244 is not operating to create additional vacuum (and noise) within the system. When pressure signal 252 from sensor 250 indicates a drop in pressure within reservoir 240, such as when one or both valves 230, 234 are opened, microcontroller 2541 will activate motor 246 to turn pump 244 on until the pressure in reservoir 240 again reaches the desired level. Sensor 250 thereby provides a closed-loop control for vacuum system 22 that maintains the desired vacuum pressure within the system without the need to continuously operate vacuum pump 244. In an alternative embodiment, microcontroller 2541 drives motor 246 to operate vacuum pump 244 based upon the anticipated need for vacuum during an operation cycle of biopsy instrument 20. Microcontroller 2541 may be preprogrammed to operate the vacuum pump at different positions in the operation cycle. Accordingly, microcontroller 2541 may increase the motor speed in anticipation of a need for vacuum such as, for example, when a user initiates a tissue sampling cycle by activating forward rocker switch 72. Microcontroller 2541 may vary the speed of motor 246 to increase or decrease vacuum depending upon the location of cutter 104 between positions one through four of the operation cycle. In one embodiment, the pressure in the reservoir 240 can be about −26.5 inches Hg (about 26.5 inches of Mercury below the local atmospheric pressure).

If desired a pressurized reservoir can be employed, and a pressure sensor and compressor can be used to maintain the pressure in the pressurized reservoir at a desired level above atmospheric pressure by using a closed loop control method as set forth above. For instance, in an alternative embodiment reservoir 240 can be a pressurized reservoir, and pump 244 can be a compressor for providing pressurized air to reservoir 240. For example, it may be desirable to pneumatically drive translation and/or rotation of the cutter with a positive pressure (or with a pressure differential employing vacuum), or to provide a pressurized flow of fluid (gas or liquid) through the cutter lumen. Alternatively, a vacuum reservoir 240 can be employed for providing vacuum in association with the cutter, and one or more separate pressurized reservoirs and associated compressors can be employed for providing motion of the cutter. In yet another embodiment, the reservoir 240 could be employed as a vacuum reservoir during one portion of the operation of the biopsy device, and as a pressurized reservoir during another portion of the operation of the biopsy device.

FIGS. 24A–24E provide a flow diagram of a control method according to the present invention for controlling the operation of cutter 104 as the cutter moves through the four distinct positions described above. The steps of the control method are represented schematically in the flow diagrams. Each box in the flow diagrams may represent one step or more than one step. For discussion purpose, each box is referred to simply as a step. Progression of the steps occurs generally in the direction of the arrows connecting the boxes. The control method described below may be used with biopsy instruments having a single motor, or two or more motors for separately driving the cutter translation and rotation, such as in the first embodiment shown in FIGS. 1–17.

Figure 24A:
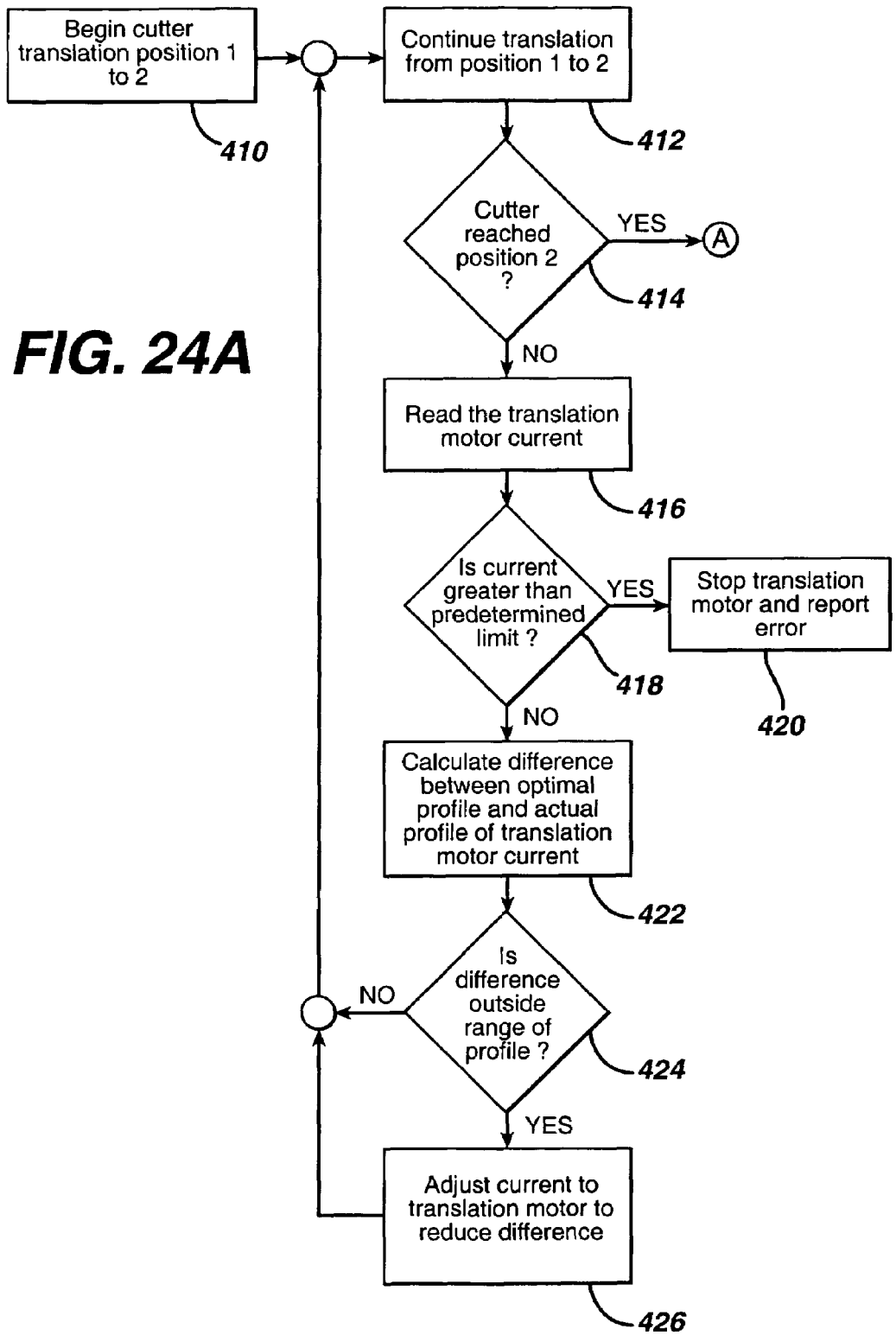
FIG. 24A is a first portion of a flow diagram pertaining to the operation of the cutter, showing the control unit logic for when the cutter translates from the first position to the second position.

Referring to FIG. 24A, step 410 represents the beginning of the control method. When biopsy instrument 20 is activated for use, such as by selecting either a sampling or manual operation mode, a control signal is transmitted through power cord 48 to switchboard 198. Switchboard 198 in turn directs that a pulse width modulation (PWM) drive signal be supplied to motor 188 to initiate rotation of translation drive shaft 160. The rotation of translation drive shaft 160 is transmitted to translation shaft 142 through the interconnection of distal end 162 and slot 158. As translation shaft 142 rotates, cam nut 136 begins to translate cutter 104 from position one to position two due to the action of cam follower pin 152 in variable pitch thread groove 144. The translation of cam nut 136 along translation shaft 142 continues in step 412.

At step 414, a predetermined time value stored in a reprogrammable memory in control unit 24 is read and compared to an accumulated time count stored in a temporary memory. The reprogrammable memory may be, for example, a "flash" memory that is contained in a microcontroller such as, for example, a PIC18F452 manufactured by Microchip Corporation. The predetermined time value corresponds to a designated position in the cutter translation path. The accumulated time count in temporary memory is updated by the microcontroller at approximately equal time intervals. In one embodiment, the time intervals can be less than or equal to about 100 milliseconds, more particularly less than or equal to about 50 milliseconds, and in one embodiment about 25 ms. The time count is derived from the actual time cutter 104 is translating through the relative positions one through four, plus (or minus) the time period calculated from a motor voltage comparison that will be described in more detail below. When the time count in temporary memory matches the predetermined time value, cutter 104 is deemed to be at position two. If the temporary time count does not match the predetermined time value for position two, then cutter 104 is not deemed to be at position two, and the operation proceeds to step 416.

At step 416, the present translation current is read from translation motor 188. At step 418, the present translation current reading is compared against a predetermined current limit stored in the flash memory. If the current reading is greater than the predetermined current limit, an error condition is determined to exist. The operation of translation motor 188 is stopped, and an error message is reported on a user interface at step 420. If at step 418 the present translation current reading is equal to or below the predetermined current limit, the control method proceeds to step 422.

Figure 25:
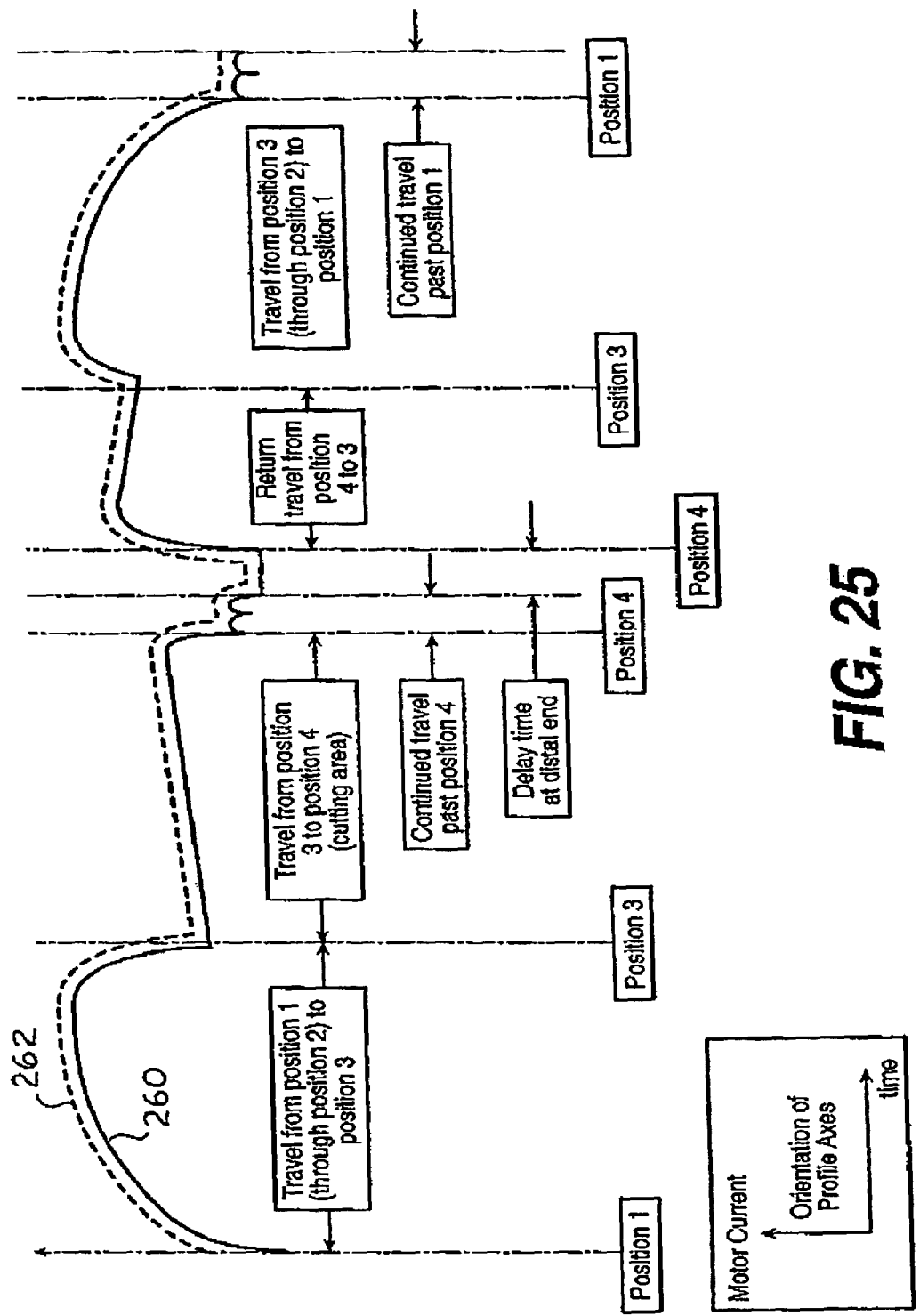
FIG. 25 is a graphical representation of an exemplary current profile for the translation motor.

At step 422, the present translation current reading is compared with a predetermined current value stored in a reprogrammable memory referred to hereinafter as the "current LUT" (Look-Up-Table). The current LUT comprises a representative current profile for each of the motors 186, 188. The current profile is derived from experimental and empirical data related to motor operation and drive current. The current profile is segmented into time intervals corresponding to the time intervals of the microprocessor, which in the exemplary embodiment described herein is 25 ms. The location in the current LUT of the predetermined current value to be used in the comparison is dependent upon the accumulated time count value at the time of the comparison. FIG. 25 illustrates an exemplary motor current profile 260 as cutter 104 traverses a complete cycle from position one to position four, and then back again to position one. In FIG. 25, current profile 260 is shown as motor current (vertical axis) verses time (horizontal axis). As shown by profile 260, the current to motor 188 varies between time increments and between each of the four cutter positions. The current LUT comprises the current level of profile 260 at each segmented time interval.

In addition to the current measurement, at step 422 the voltage of translation motor 188 is read during the off-cycle of the PWM motor drive signal. This voltage is proportional to the back electromechanical force of motor 188, as well as the linear travel speed of cutter 104. From the voltage reading, the actual position of cam nut 136 along the travel path and, thus, the position of cutter 104 can be determined. The voltage reading from motor 188 may be compared to the motor specifications, or a predetermined operational profile, to determine the actual travel speed from the voltage reading. If the motor voltage reading at the accumulated time count exceeds the anticipated voltage for the time count, then cutter 104 is deemed to be at a more advanced position in the current profile than that anticipated for the accumulated time count. Accordingly, the position of the pointer in the current LUT may be adjusted to account for the difference in distance by increasing the accumulated time count, and thereby retarding the total advance time for the cutter. Likewise, if the motor voltage reading is less than the predetermined level for the accumulated time count, then the cutter is deemed to have not traveled as far along the current profile as anticipated by the accumulated time count. The position of the pointer in the current LUT may therefore be adjusted to account for the difference in travel distance by reducing the accumulated time count and, therefore, rereading or moving backwards in the current LUT and increasing the total advance time for the cutter.

At step 424, a comparison is made to determine if the difference between the present translation current and the current value from the current LUT is outside a predetermined range, such as the range indicated by dashed line 262 in FIG. 25. If the difference between the current values is outside the predetermined range, the current to translation motor 188 is adjusted at step 426, such as by increasing or decreasing the duty cycle of the pulse width modulated motor control signal (or by changing a voltage level if an analog motor drive is employed rather than PWM). If the difference between the present translation current and the predetermined current LUT value is determined at step 424 to be within the acceptable range, then the process returns to step 412 and cutter 104 continues translating from position one to position two.

Figure 24B:
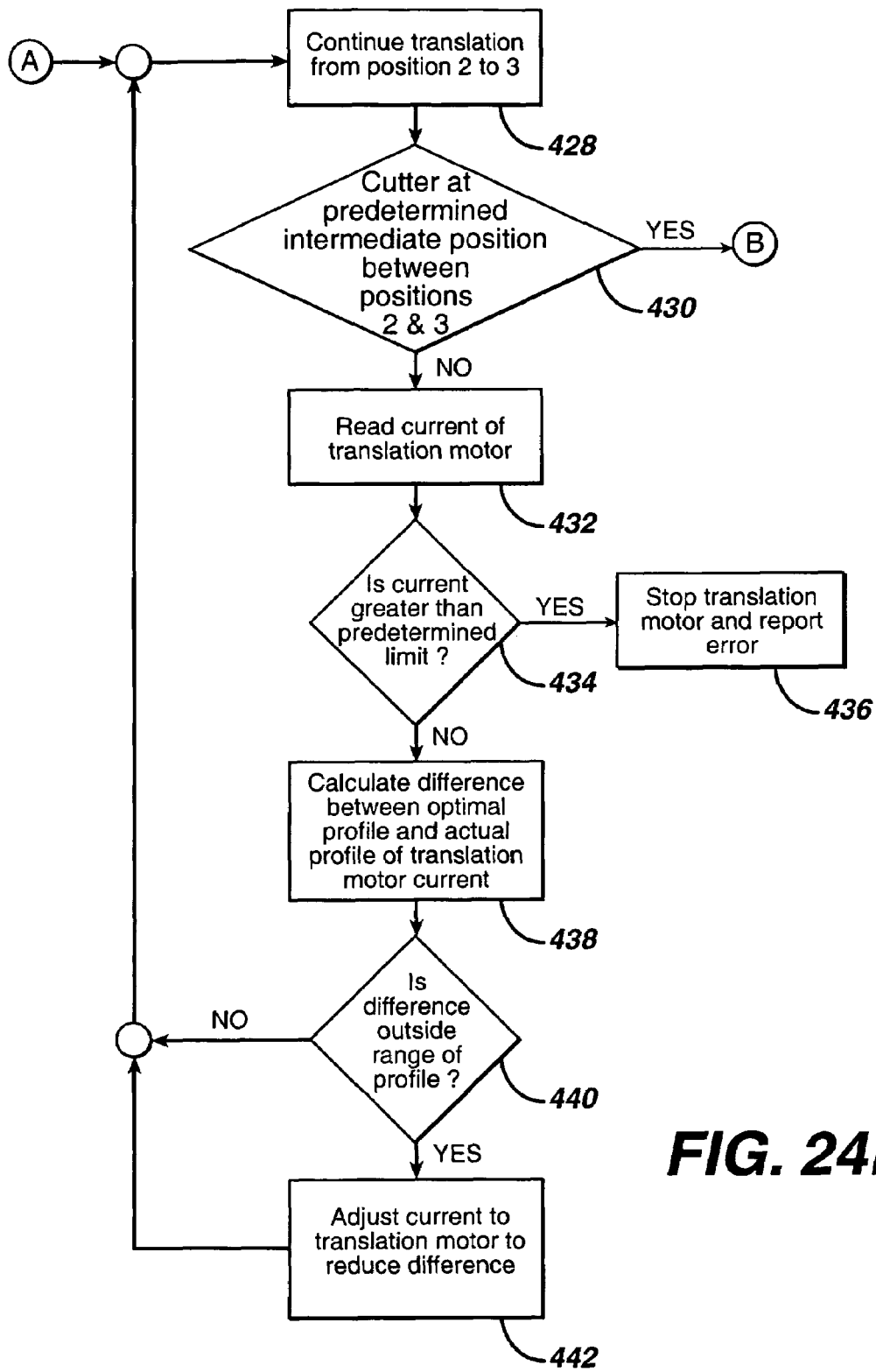
FIG. 24B is a second portion of a flow diagram pertaining to the operation of the cutter, showing the control unit logic for when the cutter translates from the second to the third position.

If at step 414 cutter 104 is deemed to be at position two, then the control method passes to step 428 shown in FIG. 24B, and the cutter continues translating from position two to position three. At step 430, a check is made to determine if cutter 104 has reached a predetermined intermediate position between position two and position three. Cutter 104 is deemed to have reached the intermediate position when the accumulated time count in temporary memory matches a predetermined time count corresponding to the intermediate position. The predetermined intermediate position is based on the actual cutter translation speed and the predetermined cutter rotation speed. The intermediate position is selected to allow a sufficient amount of time for cutter 104 to accelerate from zero to the predetermined rotation speed before cutter 104 has reached position three, after which tissue cutting begins. If at step 430 cutter 104 has not reached the intermediate position, then the present translation current from motor 188 is read at step 432.

At step 434, the present translation current is again compared to a predetermined current limit stored in the flash memory. If the present translation current reading is greater than the predetermined current limit, an error condition is determined to exist. The operation of translation motor 188 is stopped, and an error message is reported on a user interface at step 436. If at step 434 the present translation current is determined to be equal to or below the predetermined current limit, operation of instrument 20 continues at step 438. At step 438, the present translation motor current reading is again compared with a predetermined value in the current LUT. Once again, the location of the comparison value in the current LUT is dependent upon the updated accumulated time count at the time of the comparison. Also, at step 438 the present motor voltage is read and compared with the anticipated voltage based upon the updated accumulated time count. If the actual voltage reading differs from the anticipated voltage, then the accumulated time count is increased or decreased to synchronize the current LUT position with the actual position of the cutter. If at step 440 the difference between the present and predetermined current values is outside a predetermined range, the current to translation motor 188 is adjusted at step 442. If the difference from the comparison at step 440 is within the predetermined range, then cutter 104 continues translating from position two to position three at its present rate at step 428.

Figure 24C:
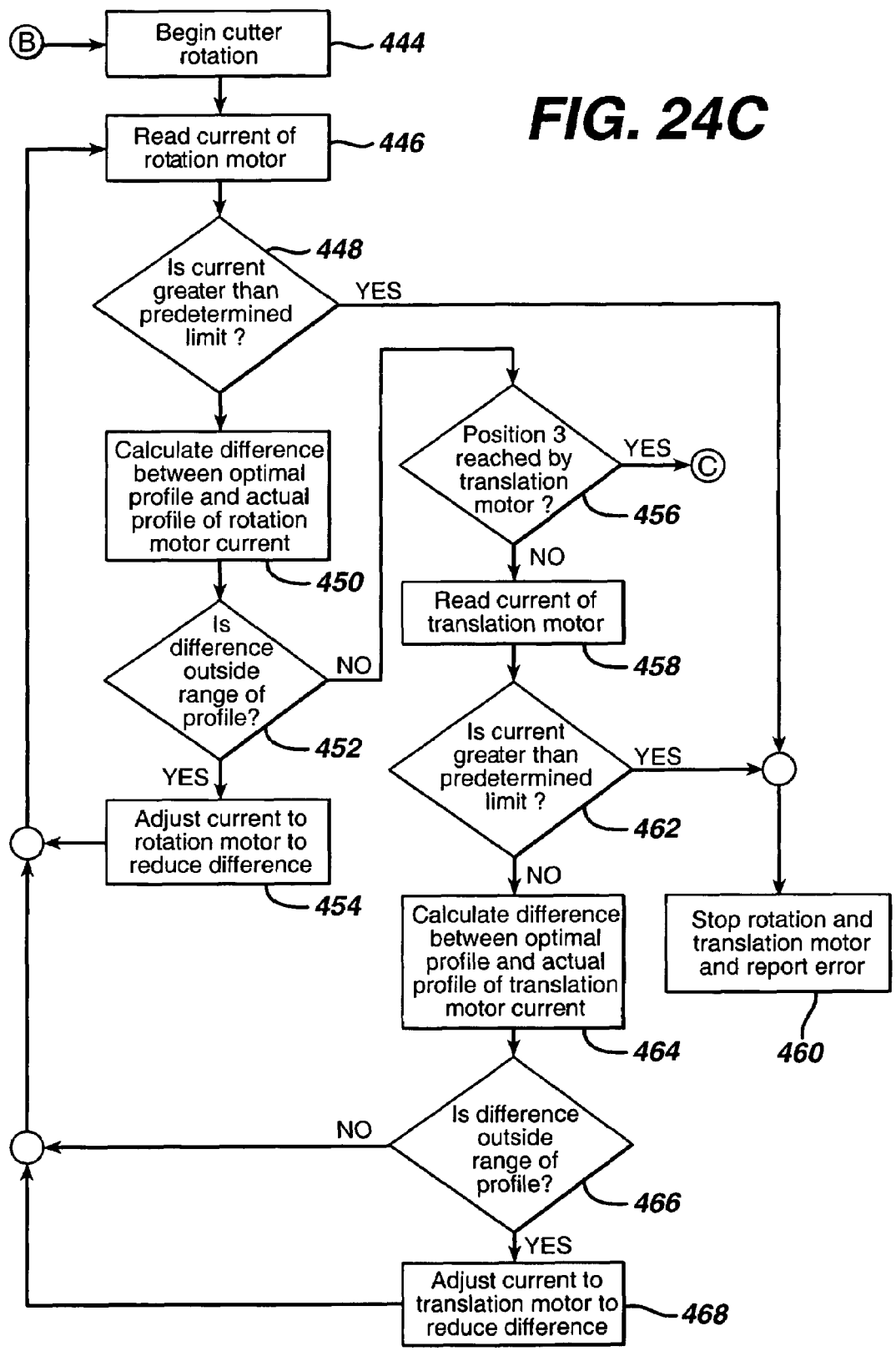
FIG. 24C is a third portion of a flow diagram pertaining to the operation of the cutter, showing additional control unit logic for when the cutter translates from the second to the third position.

If at step 430 cutter 104 is determined to have reached the intermediate point between position two and position three, then the cutter continues to translate towards position three and the rotation of the cutter is started at step 444 shown in FIG. 24C. At step 446, the present rotation current is read for rotary drive motor 186. At step 448, a comparison is made to determine if the present rotation motor current is greater than a predetermined current limit stored in the flash memory. If the present current reading is greater than the predetermined limit, then the rotation and translation motors 186, 188 are stopped at step 460, and an error condition is reported on the user interface. If the present rotation current reading is equal to or below the predetermined limit, then the operation continues to the next step. At step 450, the present rotation current reading is compared with a predetermined current value loaded into the current LUT. As mentioned above, the location of the comparison value in the current LUT is dependent upon the accumulated time count at the time of the comparison. If at step 452 the difference of the comparison is determined to be outside a predetermined range, the current to the rotation motor 186 is adjusted at step 454. If at step 452 the difference between the present current value and the predetermined current value is within a predetermined range, then rotation of cutter 104 continues.

At step 456, a predetermined time value stored in memory in the microcontroller is compared to the accumulated time count stored in the temporary memory. The accumulated time count is derived from the actual time the cutter is moving through its relative position plus (or minus) the time calculated from the motor voltage comparisons at steps 422, 438 and 464. When the accumulated time count matches the stored time count, cutter 104 is determined to be at the third position. If cutter 104 is not at the third position, the process continues to step 458, where the present translation current is read from motor 188. At step 462, the present translation current reading is compared against a predetermined current limit. If the present current reading is greater than the predetermined limit, the translation and rotation motors are stopped and an error is reported at step 460.

If the reading is equal to or below the limit, the process continues at step 464, where the present current reading is compared with a predetermined value loaded into the current LUT. The location of the comparison value in the current LUT is dependent on the updated accumulated time count at the time of the comparison. Also, at step 464 the actual motor voltage is compared with the anticipated voltage. The accumulated time count is increased or decreased as described above to account for an increase or decrease in the motor voltage corresponding to a change in the actual travel speed of cutter 104. If at step 466 the difference between the present current reading and the predetermined current value from the current LUT is determined to be within an allowable range, then translation of cutter 104 continues, and the process proceeds to step 446. If the difference from the comparison is outside the predetermined allowable range, then the current to translation motor 468 is adjusted. After this adjustment, the process continues to step 446.

Figure 24D:
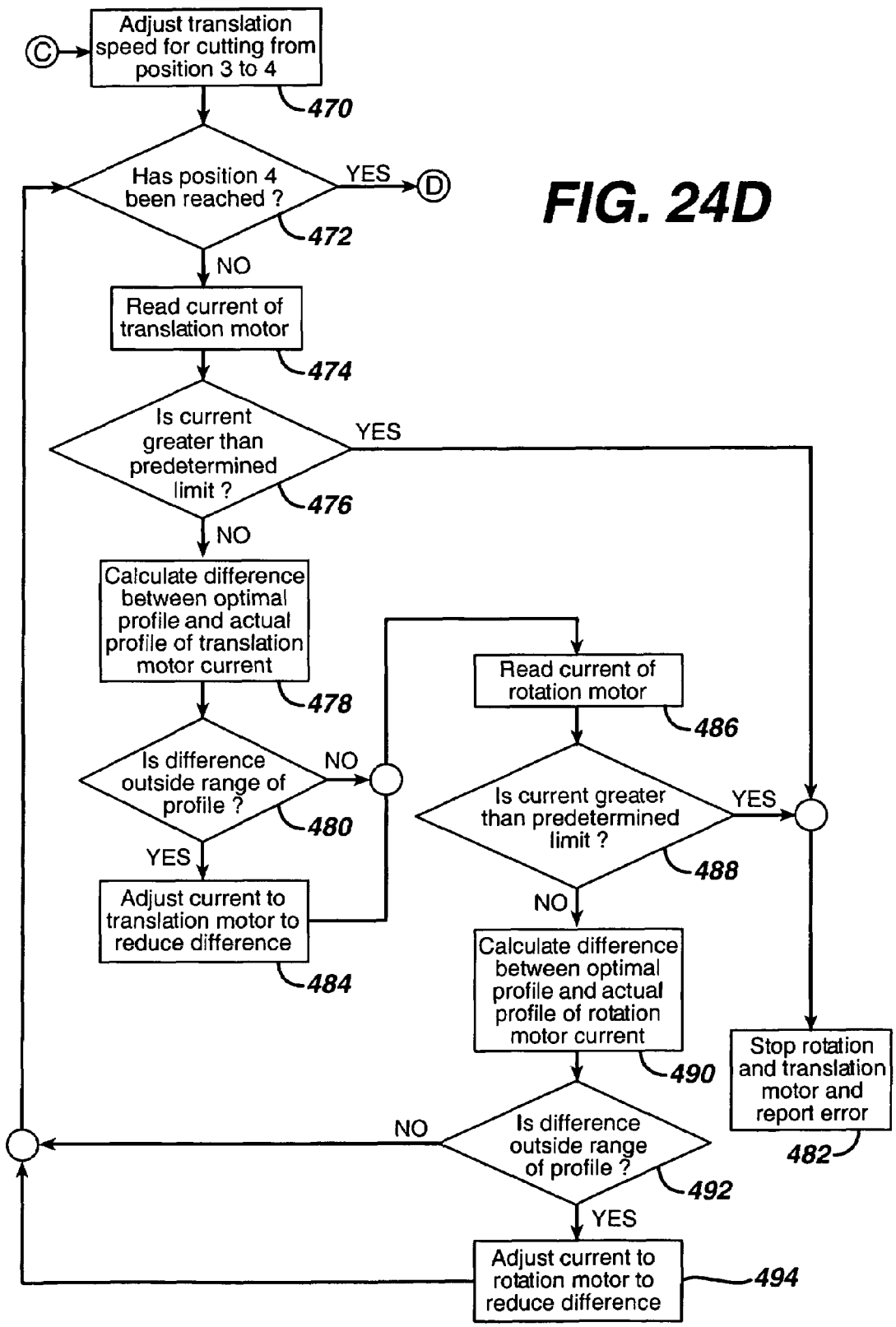
FIG. 24D is a fourth portion of a flow diagram pertaining to the operation of the cutter, showing the control unit logic for when the cutter translates from the third to the fourth position.

When it has been determined at step 456 that cutter 104 has reached position three, then the process proceeds to step 470 shown in FIG. 24D. At step 470, the translation current to motor 188 is changed to a predetermined value and stored in the memory. The changed current value continues the translation of cutter 104 towards the fourth position, but at a different velocity, typically 0.5 inches per second. At step 472, a predetermined value stored in the reprogrammable memory in the microcontroller is compared to the accumulated time count stored in the temporary memory. The time count is derived from the actual time cutter 104 is moving through its relative positions plus (or minus) the time calculated from the motor voltage comparisons. When the present time count matches the stored time count, it is deemed that the cutter is at position four.

At step 474, the present translation current is read. At step 476, the translation current reading is compared against a predetermined current limit. If the translation current reading is greater than the predetermined limit, the process moves to step 482, where the translation and rotation motors 186, 188 are stopped and an error message is displayed. If at step 476 the present translation current reading is less than or equal to the limit, the process continues to step 478. At step 478, the motor voltage is read and compared to a predetermined motor voltage level. If the voltage reading is higher than anticipated, then the accumulated time count is increased to account for an increase in travel speed. If the voltage reading is lower than anticipated, the accumulated time count is decreased to account for a decrease in the actual travel speed of the cutter. Also at step 478, the present translation current reading is compared with a predetermined value loaded into the current LUT. If at step 480 the difference between the present and predetermined current values is determined to be outside of a predefined range, the current is adjusted to the translation motor 186 at step 484. If at step 480 the difference between the present and predetermined current values is within a predetermined range, then cutter 104 continues translating and the process moves to step 486. At step 486, the present rotation current is again read, and at step 488 the latest current reading is compared against a predetermined limit. If the current reading is greater than the predetermined limit, translation and rotation motors 186, 188 are stopped and an error reported at step 482. If the present rotation current reading is equal to or below the predetermined limit, then operation continues on to the next step. At step 490, the present rotation motor current is again compared with a predetermined value loaded into the current LUT, and the difference between the two levels is calculated. If the difference in the current levels is determined at step 492 to be outside a predetermined range, then the current is adjusted to the rotation motor at step 494. If at step 492 the difference between the two current levels is determined to be within a predetermined range, then cutter rotation continues, and the process moves to step 472.

Figure 24E:
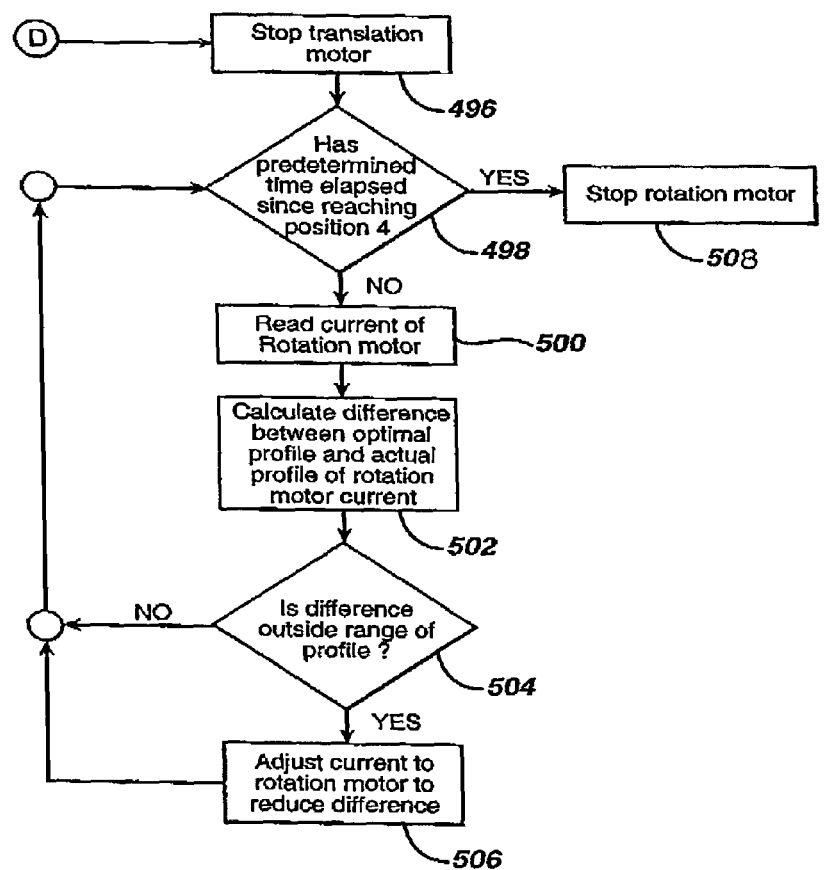
FIG. 24E is a fifth portion of a flow diagram pertaining to the operation of the cutter, showing the control unit logic for terminating operation of the cutter after the cutter has reached the fourth position.

If at step 472, cutter 104 has reached position four, then the control method continues to step 496 shown in FIG. 24E, at which point translation motor 188 is stopped. Next, at step 498, a predetermined value stored in the microcontroller is compared to the accumulated time count stored in the temporary memory. The time count is derived from the actual time the rotation motor was turned on plus (or minus) time adjustments calculated from the motor voltage comparisons. If at step 498 the time count comparison does not match the stored time count, then the actual rotation motor current is read at step 500. At step 502, the actual rotation motor current is compared with a predetermined value loaded into the current LUT, with the location of the comparison value in the current LUT being dependent on the time count interval value at the time of the comparison. If it is determined at step 504 that the difference between the actual rotation motor current and the predetermined value for the rotation current is outside a predetermined range, then the current to rotation motor 186 is adjusted at step 506. If the difference from the comparison is within the predetermined range, then the control method proceeds to step 498. At step 498, the predetermined time count is compared to the accumulated time count for rotation motor 186. If the accumulated time count exceeds the predetermined value, then the rotation motor is stopped at step 508.

While electric motors are disclosed in the embodiments described above, it will be understood that other types of motors, such as pneumatic motors could be employed. Additionally, while an outer cannula with an inner cutter is disclosed, other variations may be employed, such as an embodiment wherein a cutter is coaxially disposed about the outside of a cannula.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element disclosed may be alternatively described as a means for performing the element's function.

What is claimed:
1. A biopsy device comprising:
   an outer cannula having a lateral tissue receiving port;
   an inner tubular cutter disposed for translation within the cannula;
   a rotating member having a screw thread feature of varying pitch, wherein the rotating member is opera- tively associated with the cutter for varying the translational speed of the cutter as the tissue cutter is advanced in relation to the tissue receiving port.

2. The biopsy device of claim 1 comprising a motor for rotating the rotating member.

3. The biopsy device of claim 2 wherein the motor is an electric motor.

4. The biopsy device of claim 1 wherein the rotating member has a relatively coarse thread pitch portion and a relatively fine thread pitch portion.

5. The biopsy device of claim 1 wherein the rotating member is adapted to rotate without translation of the cutter in at least one position of the cutter.

6. The biopsy device of claim 5 wherein the rotating member is adapted to rotate without translation of the cutter when the cutter is at a position of distal most cutter travel and when the cutter is at a position of proximal most cutter travel.

7. The biopsy device of claim 5 wherein the screw thread feature is adapted at the proximal and distal ends of the screw thread feature to permit rotation of the rotating member without providing translation of the cutter.

8. The biopsy device of claim 1 comprising a cam nut supported for translation along the rotating member, wherein the cam nut engages the screw thread feature of the rotating member, and wherein the cutter is rotatably supported on the cam nut.

9. The biopsy device of claim 8 further comprising a rotation shaft for providing rotation of the cutter.

10. A biopsy device comprising:
a cannula having a lateral tissue receiving port;
a tissue cutter disposed coaxially with the cannula, the cutter adapted for translation relative to the cannula; and
a variable pitch member operatively associated with the tissue cutter for providing variation in the translational speed of the tissue cutter as the tissue cutter is advanced in relation to the tissue receiving port.

11. The biopsy device of claim 10 wherein the tissue cutter is adapted for translation and rotation relative to the cannula.

12. The biopsy device of claim 10 comprising a motor for rotating the variable pitch member.

13. The biopsy device of claim 10 wherein the variable pitch member comprises a shaft having a threaded portion of varying pitch.

14. The biopsy device of claim 10 comprising a first motor for providing rotation of the variable pitch member and a second motor for providing rotation of the cutter.

15. The biopsy device of claim 10 wherein the cutter is disposed for translation within the cannula.

16. The biopsy device of claim 10 wherein the variable pitch member comprises a relatively coarse pitch portion and a relatively fine pitch portion.

17. The biopsy device of claim 16 wherein the relatively fine pitch portion provides translation of the cutter past the tissue receiving port.

18. The biopsy device of claim 10 wherein the variable pitch member comprises a shaft having a threaded portion of varying pitch, and wherein the diameter of the shaft varies alone a length of the threaded portion.

19. A biopsy device comprising:
an outer cannula having a lateral tissue receiving port;
an inner tubular cutter disposed for translation within the cannula;
a rotating member having a screw thread feature of varying pitch, wherein the rotating member is operatively associated with the cutter for varying the translational speed of the cutter, and wherein the rotating member is adapted to rotate without translation of the cutter in at least one position of the cutter.

20. The biopsy device of claim 19 wherein the rotating member is adapted to rotate without translation of the cutter when the cutter is at a position of distal most cutter travel, and when the cutter is at a position of proximal most cutter travel.

* * * * *